(12) United States Patent
Schoenafinger et al.

(10) Patent No.: US 7,888,343 B2
(45) Date of Patent: Feb. 15, 2011

(54) SUBSTITUTED, BICYCLIC 8-PYRROLIDINOXANTHINES, AND METHODS FOR THEIR USE AS INHIBITORS OF DIPEPTIDYL PEPTIDASE

(75) Inventors: Karl Schoenafinger, Alzenau (DE); Gerhard Jaehne, Frankfurt (DE); Elisabeth Defossa, Idstein (DE); Lothar Schwink, Stadtallendorf (DE); Holger Wagner, Biberach/Mettenberg (DE); Christian Buning, Bonn (DE); Georg Tschank, Essenheim (DE); Ulrich Werner, Miehlen (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 709 days.

(21) Appl. No.: 11/624,511

(22) Filed: Jan. 18, 2007

(65) Prior Publication Data

US 2007/0197563 A1 Aug. 23, 2007

Related U.S. Application Data

(63) Continuation of application No. PCT/EP2005/008002, filed on Jul. 22, 2005.

(30) Foreign Application Priority Data

Aug. 6, 2004 (DE) ........................ 10 2004 038 268

(51) Int. Cl.
*C07D 519/00* (2006.01)
*A61K 31/522* (2006.01)
*A61P 3/06* (2006.01)
*A61P 3/10* (2006.01)
*C07D 471/04* (2006.01)
*C07D 487/04* (2006.01)

(52) U.S. Cl. .................. 514/211.09; 514/263.2; 514/263.22; 540/580; 544/268; 546/113; 548/453

(58) Field of Classification Search ................ None
See application file for complete search history.

(56) References Cited

U.S. PATENT DOCUMENTS 3,472,861 A * 10/1969 Schulz et al. ............. 546/91

7,074,798 B2 * 7/2006 Yoshikawa et al. ....... 514/263.2
7,235,538 B2 * 6/2007 Kanstrup et al. ............. 514/81
7,495,004 B2 * 2/2009 Boggs et al. .......... 514/263.21
2004/0087587 A1 * 5/2004 Himmelsbach et al. .. 514/234.5
2007/0167468 A1 * 7/2007 Schoenafinger et al. .. 514/263.2

FOREIGN PATENT DOCUMENTS

EP          1338595        10/2003
WO     WO 0063208         10/2000
WO     WO 02/068420        9/2002

OTHER PUBLICATIONS

Blandine Laferrere et al., Effects of bombesin, of a new bombesin agonist (BIM187) and a new antagonist (BIM189) on food intake in rats, in relation to cholecystokinin, European Journal of Pharmacology, (1992), vol. 215, pp. 23-28.
Corri Black, et al., Meglitinide analogues for type 2 diabetes meilitus, The Cochrane Review, (2007).
Renzo Cescato, et al., Bombesin Receptor Antagonists May Be Preferable to Agonists for Tumor Targeting, The Journal of Nuclear Medicine, 2008, vol. 49, No. 2, pp. 318-326.

* cited by examiner

*Primary Examiner*—Mark L Berch
(74) *Attorney, Agent, or Firm*—Scully, Scott, Murphy & Presser, P.C.

(57) ABSTRACT

The present invention involves substituted bicyclic 8-pyrrolidinoxanthines and their derivatives of formula I:

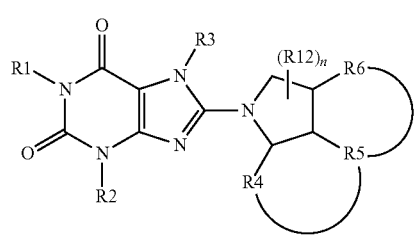

wherein the various R groups are defined herein. The present invention also comprises pharmaceutical compositions comprising them as well as processes for the preparation of these compounds and methods for the treatment of metabolic disorders such as type-2 diabetes, insulin resistance, hyperglycemia, arteriosclerosis diseases and the like through the administration of said compositions.

8 Claims, No Drawings

SUBSTITUTED, BICYCLIC 8-PYRROLIDINOXANTHINES, AND METHODS FOR THEIR USE AS INHIBITORS OF DIPEPTIDYL PEPTIDASE

CROSS-REFERENCE TO RELATED APPLICATIONS

This application is a continuation of International Patent Application No. PCT/EP2005/008002 filed on Jul. 22, 2005 which is incorporated herein by reference in its' entirety which also claims the benefit of priority of German Patent Application No. 10/2004 038 268.9 filed on Aug. 6, 2004.

FIELD OF THE INVENTION

The present invention relates generally to compounds for the treatment of metabolic disorders such as type-2 diabetes, hyperglycemia, atherosclerotic diseases and the like. Specifically, the present invention relates to compounds that inhibit the activity of dipeptidyl peptidase IV (DPP-IV) and are thus very suitable for lowering the blood glucose level. More specifically, the present invention relates to substituted bicyclic 8-pyrrolidinalkylthioxanthines, their physiologically tolerated salts and functional derivatives and their therapeutic use as blood sugar-lowering agents among others.

BACKGROUND OF THE INVENTION

Inhibition of DPP-IV increases the circulating half-life of the incretin hormones, GLP-1 and GIP, and improving glucose tolerance in Type II diabetics. Complete inhibition of DPP-IV does not appear to be necessary as 2- to 3-fold increases in plasma concentrations of GLP-1 have been achieved in mice with inactivation of 84% to 96% of plasma DPP-IV. Thus, there has been much interest in developing DPP-IV inhibitors for the treatment of Type II diabetes and other metabolic disorders.

DPP-IV exists as both a membrane-spanning form present in cells throughout the body and a soluble circulating form. Both forms of DPP-IV have identical enzymatic activity and cleave a wide range of bioactive peptides in vitro, including hormones, neuropeptides, and chemokines. One potential regulatory role of DPP-IV is the inactivation of GHRH through cleavage of the active form, GHRH (1-44)-$NH_2$, to the N-terminally shortened inactive form, GHRH (3-44)-$NH_2$, While trypsin-like degradation of GHRH also occurs, in vitro studies using GHRH analogs designed to resist cleavage at the N-terminus have demonstrated that the primary degradation of GHRH is via DPP-IV. Substitution of Ala2 with Dali prevents DPP-IV proteolysis and administration of this analog increases GH release in swine up to 2-fold. The His1, Val2 analog of GHRH is also not degraded by DPP-IV in vitro, and it demonstrates increased plasma stability over native GHRH. GHRH analogs containing the His1, Val2 substitutions were 5.4- to 12.5-fold more potent than native GHRH in release of GH in swine. Thus, inhibition of DPP-IV in vivo may increase endogenous concentrations of GHRH and enhance GH secretion.

Compounds of similar structure have been described in the prior art such as the bicyclic xanthine derivatives and their use as DDPIV inhibitors described in U.S. Pat. No. 7,074,798 to Yoshikawa et. al. which is hereby incorporated by reference.

SUMMARY OF THE INVENTION

The present invention involves substituted bicyclic 8-pyrrolidinoxanthines and their derivatives of formula I:

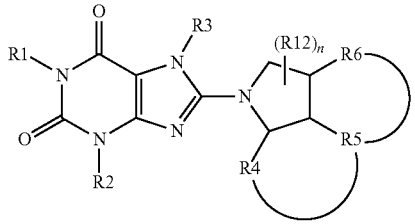

wherein the various R groups are hereinafter defined. The present invention also comprises pharmaceutical compositions comprising them as well as processes for the preparation of these compounds and methods for the treatment of metabolic disorders through their administration such as type-2 diabetes, insulin resistance, hyperglycemia, arteriosclerotic diseases and the like.

DETAILED DESCRIPTION OF THE INVENTION

The present invention involves substituted bicyclic 8-pyrrolidinoxanthines and their derivatives as well as pharmaceutical compositions comprising them, processes for the preparation of these compounds and methods for their use in the treatment of metabolic disorders such as type-2 diabetes, insulin resistance, hyperglycemia, arteriosclerotic diseases and the like.

These compounds comprise substituted bicyclic 8-pyrrolidinoxanthines and their derivatives as defined by formula I:

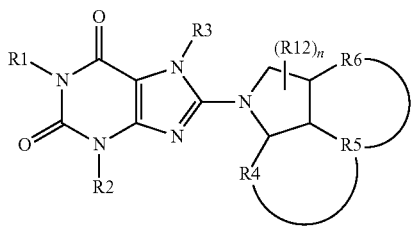

wherein the various R groups are hereinafter defined as follows:

R1, R2 and, R3 are independently selected from the group consisting of H, ($C_1$-$C_{10}$)-alkyl, ($C_3$-$C_{10}$)-cycloalkyl, ($C_2$-$C_{10}$)-alkenyl, ($C_2$-$C_{10}$)-alkynyl, ($C_6$-$C_{10}$)-aryl and ($C_6$-$C_{10}$)-heterocycle, where the alkyl, cycloalkyl, alkenyl, alkynyl, aryl and heterocyclic R groups may be substituted one or more times by F, Cl, Br, I, CN, $NO_2$, SH, OH, ($C_1$-$C_6$)-alkyl, —$CF_3$, —$OCF_3$, —$SCF_3$, ($C_2$-$C_6$)-alkenyl, ($C_2$-$C_6$)-alkynyl, OR7, OP(O)(OR7)$_2$, NR7R8, NR7CONR7R8, COR7, OCOR7, OCOOR7, COOR7, CONR7R8, OCONR7R8, ($C_1$-$C_6$)-alkylene-OR7, ($C_1$-$C_6$)-alkylene-NR7R8, ($C_1$-$C_6$)-alkylene-NR7$SO_2$R7, ($C_1$-$C_6$)-alkylene-SR7, alkylene-S(O)R7, alkylene-S(O)$_2$R7, alkylene-S(O)$_2$NR7R8, ($C_1$-$C_6$)-alkylene-COR7, ($C_1$-$C_6$)-alkylene-COOR7, ($C_1$-$C_6$)-alkylene-CONR7R8, SR7, SOR7, $SO_2$R7, $SO_2$NR7R8, NR7$SO_2$R7, ($C_1$-$C_6$)-alkylene-($C_3$-$C_{10}$)-cycloalkyl, ($C_1$-$C_6$)-alkylene-($C_6$-$C_{10}$)-aryl, ($C_1$-$C_6$)-alkylene-heterocycle, ($C_3$-$C_{10}$)-cycloalkyl, ($C_6$-$C_{10}$)-aryl or heterocycle;

R7 and R8 are independently selected from the group consisting of H, ($C_1$-$C_6$)-alkyl, —$CF_3$, ($C_3$-$C_{10}$)-cycloalkyl, ($C_6$-$C_{10}$)-aryl, heterocycle, ($C_1$-$C_6$)-alkylene-CONR9R10, CONR9R10, ($C_1$-$C_6$)-alkylene-COOR9, COOR9, COR9, ($C_1$-$C_6$)-alkylene-COR9, ($C_1$-$C_6$)-alkylene-OR9, ($C_1$-$C_6$)-alkylene-NR9R10, ($C_1$-$C_6$)-alkylene-SR9, ($C_1$-$C_6$)-alkylene-S(O)R9, ($C_1$-$C_6$)-alkylene-S(O)$_2$R9, S(O)R9, S(O)$_2$R9, ($C_1$-$C_4$)-alkylene-($C_6$-$C_{10}$)-aryl or ($C_1$-$C_4$)-alkylene-heterocycle;

R9 and R10 are independently selected from the group consisting of H, ($C_1$-$C_6$)-alkyl, ($C_1$-$C_6$)-alkylene-($C_6$-$C_{10}$)-aryl, —($C_6$-$C_{10}$)-aryl, —($C_6$-$C_{10}$)-heterocycle, ($C_1$-$C_6$)-alkylene-heterocycle;

R4 and R5 together form a 3- to 5-membered alkylene chain in which one CH$_2$ group is replaced by NR11, where R6 is equal to H or R12, or R5 and R6 together form a 3- to 5-member alkylene chain in which one CH$_2$ group is replaced by NR11, where R4 is equal to H or R12; where the 3- to 5-membered alkylene chain may be substituted in each case one or more times by F, Cl, Br, I, ($C_1$-$C_6$)-alkyl, ($C_3$-$C_8$)-cycloalkyl, NH$_2$, NH($C_1$-$C_6$)-alkyl, NH($C_3$-$C_7$)-cycloalkyl, N(($C_1$-$C_6$)-alkyl)$_2$ or O—($C_1$-$C_6$)-alkyl, where the alkyl groups may be substituted one or more times by F, Cl, Br, I;

R11 is hydrogen, ($C_1$-$C_6$)-alkyl, ($C_3$-$C_8$)-cycloalkyl, ($C_1$-$C_4$)-alkylene-aryl or ($C_1$-$C_4$)-alkylene-heterocycle;

R12 is F, Cl, Br, I, ($C_1$-$C_6$)-alkyl, ($C_3$-$C_8$)-cycloalkyl, NH$_2$, NH($C_1$-$C_6$)-alkyl, NH($C_3$-$C_7$)-cycloalkyl, N(($C_1$-$C_6$)-alkyl)$_2$ or O—($C_1$-$C_6$)-alkyl, where the alkyl groups may be substituted one or more times by F, Cl, Br, I;

N is 0, 1, 2, 3 or 4;

In some preferred embodiments, in formula I the symbol "*" shows the point of attachment of the R-group substituent A on the xanthine molecule which is further defined as follows

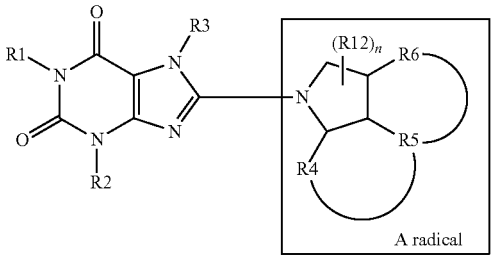

I

As will be more specifically disclosed herein, A can be further defined as specific sub-groups. For example, in two (2) embodiments, A has the meaning:

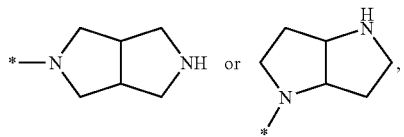

The compound may exist as physiologically tolerated salt thereof.

Preferably, the present invention comprises compounds of the formula I in which one or more R-groups are defined as follows:

R1, R2 and R3 are independently selected from the group consisting of H, ($C_1$-$C_{10}$)-alkyl, ($C_3$-$C_{10}$)-cycloalkyl, ($C_2$-$C_{10}$)-alkenyl, ($C_2$-$C_{10}$)-alkynyl, ($C_6$-$C_{10}$)-aryl, ($C_6$-$C_{10}$)-heterocyclyl, where the alkyl, cycloalkyl, alkenyl, alkynyl, aryl and the heterocycle R-groups may be substituted one or more times by F, Cl, Br, I, CN, NO$_2$, SH, OH, ($C_1$-$C_6$)-alkyl, —CF$_3$, —OCF$_3$, —SCF$_3$, ($C_2$-$C_6$)-alkenyl, ($C_2$-$C_6$)-alkynyl, OR7, OP(O)(OR7)$_2$, NR7R8, NR7CONR7R8, COR7, OCOR7, OCOOR7, COOR7, CONR7R8, OCONR7R8, ($C_1$-$C_6$)-alkylene-OR7, ($C_1$-$C_6$)-alkylene-NR7R8, ($C_1$-$C_6$)-alkylene-NR7SO$_2$R7, ($C_1$-$C_6$)-alkylene-SR7, alkylene-S(O)R7, alkylene-S(O)$_2$R7, alkylene-S(O)$_2$NR7R8, ($C_1$-$C_6$)-alkylene-COR7, ($C_1$-$C_6$)-alkylene-COOR7, ($C_1$-$C_6$)-alkylene-CONR7R8, SR7, SOR7, SO$_2$R7, SO$_2$NR7R8, NR7SO$_2$R7, ($C_1$-$C_6$)-alkylene-($C_3$-$C_{10}$)-cycloalkyl, ($C_1$-e)-alkylene-($C_6$-$C_{10}$)-aryl, ($C_1$-$C_6$)-alkylene-heterocycle, ($C_3$-$C_{10}$)-cycloalkyl, ($C_6$-$C_{10}$)-aryl-heterocycle;

R7 and R8 are independently selected from the group consisting H, ($C_1$-$C_6$)-alkyl, ($C_3$-$C_{10}$)-cycloalkyl, ($C_6$-$C_{10}$)-aryl, ($C_6$-$C_{10}$)-heterocycle, ($C_1$-$C_6$)-alkylene-CONR9R10, ($C_1$-$C_6$)-alkylene-COOR9, ($C_1$-$C_6$)-alkylene-COR9, ($C_1$-$C_6$)-alkylene-OR9, ($C_1$-$C_6$)-alkylene-NR9R10, ($C_1$-$C_6$)-alkylene-SR9, ($C_1$-$C_6$)-alkylene-S(O)R9, ($C_1$-$C_6$)-alkylene-S(O)$_2$R9, ($C_1$-$C_4$)-alkylene-($C_6$-$C_{10}$)-aryl or ($C_1$-$C_4$)-alkylene-heterocycle;

R9 and R10 are independently selected from the group consisting of H, ($C_1$-$C_6$)-alkyl, ($C_1$-$C_6$)-alkylene-($C_6$-$C_{10}$)-aryl, ($C_1$-$C_6$)-alkylene-heterocycle;

wherein R-group A, generically defined as

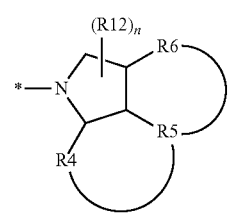

A

Further comprises one of the following structures A1 to A6

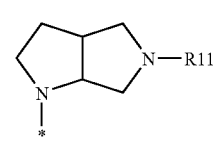

A1

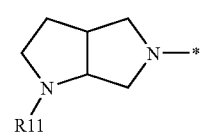

A2

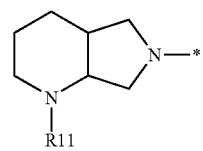

A3

-continued

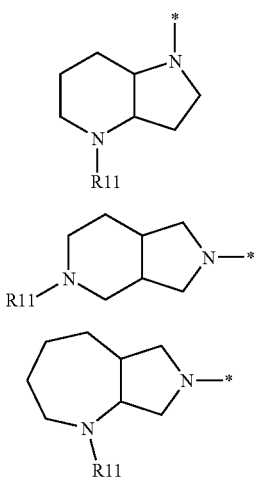

A4

A5

A6 wherein the carbon atoms in structures A1 to A6 may be substituted one to four times by F, Cl, Br, I, $(C_1-C_6)$-alkyl, $(C_3-C_8)$-cycloalkyl, $NH_2$, $NH(C_1-C_6)$-alkyl, $NH(C_3-C_7)$-cycloalkyl, $N((C_1-C_6)$-alkyl$)_2$ or $O-(C_1-C_6)$-alkyl, where the alkyl groups may be substituted one or more times by F, Cl, Br, I;

R11 hydrogen, $(C_1-C_6)$-alkyl, $(C_3-C_8)$-cycloalkyl, $(C_1-C_4)$-alkylene-aryl or $(C_1-C_4)$-alkylene-heterocycle;

The compound may exist as physiologically tolerated salt thereof

More preferably the present invention comprises compounds of formula I in which one or more of the R-groups are further defined as follows:

R1, R2 and R3 are independently selected from the group consisting of H, $(C_1-C_{10})$-alkyl, $(C_3-C_{10})$-cyclically, $(C_2-C_{10})$-alchemy, $(C_2-C_{10})$-alkynes, $(C_6-C_{10})$-aryl, $(C_6-C_{10})$-heterocyclic, where the alkyl, cyclically, alchemy, alkynes, aryl and the heterocycle R-groups may be substituted one or more times by F, Cl, Br, CN, OH, $(C_1-C_6)$-alkyl, $-CF_3$, $-OCF_3$, $-SCF_3$, $(C_2-C_6)$-alkenyl, $(C_2-C_6)$-alkynyl, OR7, NR7R8, NR7CONR7R8, COR7, COOR7, CONR7R8, $(C_1-C_6)$-alkylene-OR7, $(C_1-C_6)$-alkylene-NR7R8, $(C_1-C_6)$-alkylene-NR7SO$_2$R7, $(C_1-C_6)$-alkylene-SR7, alkylene-S(O)R7, alkylene-S(O)$_2$R7, alkylene-S(O)$_2$NR7R8, $(C_1-C_6)$-alkylene-COR7, $(C_1-C_6)$-alkylene-COOR7, $(C_1-C_6)$-alkylene-CONR7R8, SR7, SOR7, SO$_2$R7, SO$_2$NR7R8, NR7SO$_2$R7, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocycle, $(C_3-C_{10})$-cycloalkyl, $(C_6-C_{10})$-aryl or $(C_6-C_{10})$-heterocycle;

R7 and R8 are independently selected from the group consisting of H, $(C_1-C_6)$-alkyl, $(C_3-C_{10})$-cycloalkyl, $(C_6-C_{10})$-aryl, heterocyclyl, $(C_1-C_6)$-alkylene-CONR9R10, $(C_1-C_6)$-alkylene-COOR9, $(C_1-C_6)$-alkylene-COR9, $(C_1-C_6)$-alkylene-OR9, $(C_1-C_6)$-alkylene-NR9R10, $(C_1-C_4)$-alkylene-$(C_6-C_{10})$-aryl or $(C_1-C_4)$-alkylene-heterocycle;

R9 and R10 are independently selected from the group consisting of independently of one another H, $(C_1-C_6)$-alkyl, $(C_1-C_6)$-alkylene-$(C_6-C_{10})$-aryl, $(C_1-C_6)$-alkylene-heterocyclyl;

the R-group A generically comprises

A

And, more particularly, is one of the following structures A1 to A6

A1

A2

A3

A4

A5

A6 wherein the carbon atoms in structures A1 to A6 may be substituted one to four times by F, Cl, Br, I, $(C_1-C_6)$-alkyl, $(C_3-C_8)$-cycloalkyl, $NH_2$, $NH(C_1-C_6)$-alkyl, $NH(C_3-C_7)$-cycloalkyl, $N((C_1-C_6)$-alkyl$)_2$ or $O-(C_1-C_6)$-alkyl, and the alkyl groups may be substituted one or more times by F, Cl, Br, I;

R11 is hydrogen, and;

The compound may exist as a physiologically tolerated salt thereof.

Most preferred, are the compounds of the formula wherein one or more of the R-group substitutents have the following meaning:

R1, R2 and R3 are independently selected from the group consisting of H, $(C_1$-$C_{10})$-alkyl, $(C_3$-$C_{10})$-cycloalkyl, $(C_2$-$C_{10})$-alkenyl, $(C_2$-$C_{10})$-alkynyl, $(C_6$-$C_{10})$-aryl, heterocycle, where alkyl, cycloalkyl, alkenyl, alkynyl, aryl and heterocycle R-groups may be substituted one or more times by F, Cl, CN, $(C_1$-$C_6)$-alkyl, —$CF_3$, —$OCF_3$, —$SCF_3$, OR7, NR7R8, COR7, COOR7, CONR7R8, $(C_1$-$C_6)$-alkylene-OR7, $(C_1$-$C_6)$-alkylene-NR7R8, $(C_1$-$C_6)$-alkylene-NR7SO$_2$R7, SR7, SOR7, SO$_2$R7, SO$_2$NR7R8, NR7SO$_2$R7, $(C_1$-$C_6)$-alkylene-$(C_6$-$C_{10})$-aryl, $(C_1$-$C_6)$-alkylene-heterocycle, $(C_3$-$C_{10})$-cycloalkyl, $(C_6$-$C_{10})$-aryl or $(C_6$-$C_{10})$-heterocycle;

R7 and R8 are independently selected from the group consisting of H, $(C_1$-$C_6)$-alkyl, $(C_3$-$C_{10})$-cycloalkyl, $(C_6$-$C_{10})$-alkylene-$(C_6$-$C_{10})$-aryl or $(C_1$-$C_4)$-alkylene-heterocycle;

Wherein the portion of formula I represented by structure A

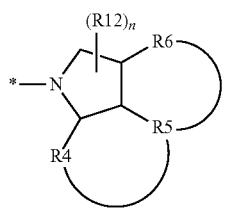

A is comprised of one of the following structures A1 to A4

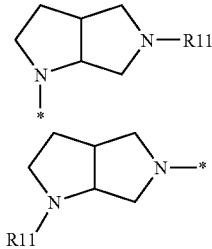

A1

A3

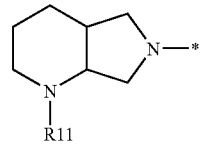

A4

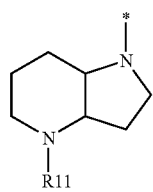

wherein the carbon atoms in structures A1 to A4 may be substituted one to four times by F, Cl, Br, I, $(C_1$-$C_6)$-alkyl, $(C_3$-$C_8)$-cycloalkyl, NH$_2$, NH$(C_1$-$C_6)$-alkyl, NH$(C_3$-$C_7)$-cycloalkyl, N$((C_1$-$C_6)$-alkyl)$_2$ or O—$(C_1$-$C_6)$-alkyl, where the alkyl groups may be substituted one or more times by F, Cl, Br, I;

R11 hydrogen, and;

The compound may exist as a physiologically tolerated salt thereof.

More preferably, compounds of the formula I are comprised of R-group substitutents which have the following meaning:

R1, R2 and R3 are independently selected from the group consisting of H, $(C_1$-$C_{10})$-alkyl, $(C_3$-$C_{10})$-cyclically, $(C_2$-$C_{10})$-alkenyl, $(C_2$-$C_{10})$-alkynyl, $(C_6$-$C_{10})$-aryl, heterocycle, where the alkyl, cycloalkyl, alkenyl, alkynyl, aryl and heterocyclic radicals may be substituted one or more times by F, Cl, CN, $(C_1$-$C_6)$-alkyl, —$CF_3$, —$OCF_3$, —$SCF_3$, OR7, NR7R8, COR7, COOR7, CONR7R8, $(C_1$-$C_6)$-alkylene-OR7, $(C_1$-$C_6)$-alkylene-NR7R8, $(C_1$-$C_6)$-alkylene-NR7SO$_2$R7, SR7, SOR7, SO$_2$R7, SO$_2$NR7R8, NR7SO$_2$R7, $(C_1$-$C_6)$-alkylene-$(C_6$-$C_{10})$-aryl, $(C_1$-$C_6)$-alkylene-heterocycle, $(C_3$-$C_{10})$-cycloalkyl, $(C_6$-$C_{10})$-aryl or $(C_6$-$C_{10})$-heterocycle;

R7 and R8 are independently selected from the group consisting of H, $(C_1$-$C_6)$-alkyl, $(C_3$-$C_{10})$-cycloalkyl, $(C_6$-$C_{10})$-alkylene-$(C_6$-$C_{10})$-aryl or $(C_1$-$C_4)$-alkylene-heterocycle;

wherein the portion of formula I represented by structure A comprises

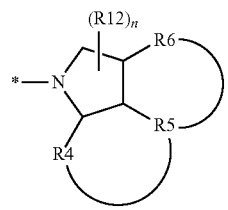

A which more specifically comprises one of the following structures A1, A2 or A3

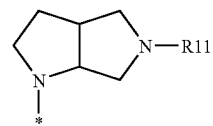

A1

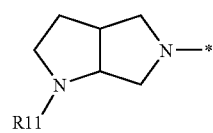

A2

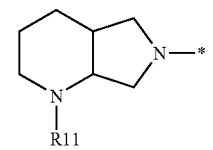

A3 wherein the carbon atoms of structures A1 to A6 may be substituted one to four times by F, Cl, Br, I, $(C_1$-$C_6)$-alkyl, $(C_3$-$C_8)$-cycloalkyl, NH$_2$, NH$(C_1$-$C_6)$-alkyl, NH$(C_3$-$C_7)$-cycloalkyl, N$((C_1$-$C_6)$-alkyl)$_2$ or O—$(C_1$-$C_6)$-alkyl, where the alkyl groups may be substituted one or more times by F, Cl, Br, I; and R11 is hydrogen;

The compound may exist as a physiologically tolerated salt thereof.

The invention also relates to compounds of the formula I in the form of its' racemates, racemic mixtures and pure enantiomers and to its' diastereomers and mixtures thereof.

If radicals or substitutents may occur more than once in the compounds of the formula I, they may all, independently of one another, have the stated meanings and be identical or different.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in non-therapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives include pro-drugs of the compounds of the invention. Such pro-drugs can be metabolized in vivo to a compound of the invention. These pro-drugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

Alkyl means a straight-chain or branched hydrocarbon chain having one or more carbons, such as, for example, methyl, ethyl, isopropyl, tert-butyl, hexyl.

The alkyl groups may be substituted one or more times by suitable groups such as, for example:

F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, cycloalkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle; $PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—$(CH_2)_n$-aryl, S—$(CH_2)_n$-heterocycle, SO—($C_1$-$C_6$)-alkyl, SO—$(CH_2)_n$-aryl, SO—$(CH_2)_n$-heterocycle, $SO_2$—($C_1$-$C_6$)-alkyl, $SO_2$—$(CH_2)_n$-aryl, $SO_2$—$(CH_2)_n$-heterocycle, $SO_2$—NH$(CH_2)_n$-aryl, $SO_2$—NH$(CH_2)_n$-heterocycle, $SO_2$—N($C_1$-$C_6$)-alkyl)$(CH_2)_n$-aryl, $SO_2$—N($C_1$-$C_6$)-alkyl)$(CH_2)_n$-heterocycle, $SO_2$—N(($CH_2)_n$-aryl)$_2$, $SO_2$—N(($CH_2)_n$-(heterocycle))$_2$ where n may be 0-6, and the aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$; C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl —CO—($C_1$-$C_6$)-alkyl, N($C_1$-$C_6$)-alkyl —COO—($C_1$-$C_6$)-alkyl, N($C_1$-$C_6$)-alkyl —CO-aryl, N($C_1$-$C_6$)-alkyl —CO-heterocycle, N($C_1$-$C_6$)-alkyl —COO-aryl, N($C_1$-$C_6$)-alkyl —COO-heterocycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—$(CH_2)_n$-aryl, O—$(CH_2)_n$-heterocycle, where n may be 0-6, where the aryl radical or heterocyclic radical may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

Alkenyl means a straight-chain or branched hydrocarbon chain having two or more carbons and one or more double bonds, such as, for example, vinyl, allyl, pentenyl, 2-methyl-but-2-en-4-yl.

The alkenyl groups may be substituted one or more times by suitable groups such as, for example: F, Cl, Br, I, $CF_3$, $NO_2$, $N_3$, CN, COOH, COO($C_1$-$C_6$)alkyl, $CONH_2$, CONH ($C_1$-$C_6$)alkyl, CON[($C_1$-$C_6$)alkyl]$_2$, cycloalkyl, ($C_1$-$C_{10}$)-alkyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle; $PO_3H_2$, $SO_3H$, $SO_2$—$NH_2$, $SO_2NH$($C_1$-$C_6$)-alkyl, $SO_2N$[($C_1$-$C_6$)-alkyl]$_2$, S—($C_1$-$C_6$)-alkyl, S—$(CH_2)_n$-aryl, S—$(CH_2)_n$-heterocycle, SO—($C_1$-$C_6$)-alkyl, SO—$(CH_2)_n$-aryl, SO—$(CH_2)_n$-heterocycle, $SO_2$—($C_1$-$C_6$)-alkyl, $SO_2$—$(CH_2)_n$-aryl, $SO_2$—$(CH_2)_n$-heterocycle, $SO_2$—NH $(CH_2)_n$-aryl, $SO_2$—NH$(CH_2)_n$-heterocycle, $SO_2$—N($C_1$-$C_6$)-alkyl)$(CH_2)_n$-aryl, $SO_2$—N($C_1$-$C_6$)-alkyl)$(CH_2)_n$-heterocycle, $SO_2$—N(($CH_2)_n$-aryl)$_2$, $SO_2$—N(($CH_2)_n$-(heterocycle))$_2$ where n may be 0-6, and the aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$; C(NH)($NH_2$), $NH_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl —CO—($C_1$-$C_6$)-alkyl, N($C_1$-$C_6$)-alkyl —COO—($C_1$-$C_6$)-alkyl, N($C_1$-$C_6$)-alkyl —CO-aryl, N($C_1$-$C_6$)-alkyl —CO-heterocycle, N($C_1$-$C_6$)-alkyl —COO-aryl, N($C_1$-$C_6$)-alkyl —COO-heterocycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—(CH$_2$)$_n$-aryl, O—(CH$_2$)$_n$-heterocycle, where n may be 0-6, where the aryl radical or heterocyclic radical may be substituted one to 3 times by F, Cl, Br, I, OH, CF$_3$, NO$_2$, CN, OCF$_3$, O—($C_1$-$C_6$)-alkyl, ($C_1$-$C_6$)-alkyl, NH$_2$, NH($C_1$-$C_6$)-alkyl, N(($C_1$-$C_6$)-alkyl)$_2$, SO$_2$—CH$_3$, COOH, COO—($C_1$-$C_6$)-alkyl, CONH$_2$.

Alkynyl means a straight-chain or branched hydrocarbon chain having two or more carbons and one or more triple bonds, such as, for example, ethynyl, propynyl, butynyl, hexynyl.

The alkynyl groups may be substituted one or more times by suitable groups such as, for example: F, Cl, Br, I, CF$_3$, NO$_2$, N$_3$, CN, COOH, COO($C_1$-$C_6$)alkyl, CONH$_2$, CONH($C_1$-$C_6$)alkyl, CON[($C_1$-$C_6$)alkyl]$_2$, cycloalkyl, ($C_2$-$C_6$)-alkenyl, ($C_1$-$C_{10}$)-alkyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle; PO$_3$H$_2$, SO$_3$H, SO$_2$—NH$_2$, SO$_2$NH($C_1$-$C_6$)-alkyl, SO$_2$N[($C_1$-$C_6$)-alkyl]$_2$, S—($C_1$-$C_6$)-alkyl, S—(CH$_2$)$_n$-aryl, S—(CH$_2$)$_n$-heterocycle, SO—($C_1$-$C_6$)-alkyl, SO—(CH$_2$)$_n$-aryl, SO—(CH$_2$)$_n$-heterocycle, SO$_2$—($C_1$-$C_6$)-alkyl, SO$_2$—(CH$_2$)$_n$-aryl, SO$_2$—(CH$_2$)$_n$-heterocycle, SO$_2$—NH(CH$_2$)$_n$-aryl, SO$_2$—NH(CH$_2$)$_n$-heterocycle, SO$_2$—N($C_1$-$C_6$)-alkyl)(CH$_2$)$_n$-aryl, SO$_2$—N($C_1$-$C_6$)-alkyl)(CH$_2$)$_n$-heterocycle, SO$_2$—N((CH$_2$)$_n$-aryl)$_2$, SO$_2$—N((CH$_2$)$_n$-(heterocycle)$_2$ where n may be 0-6, and the aryl radical or heterocyclic radical may be substituted up to twice by F, Cl, Br, OH, CF$_3$, NO$_2$, CN, OCF$_3$, O—($C_1$-$C_6$)-alkyl, ($C_1$-$C_6$)-alkyl, NH$_2$; C(NH)(NH$_2$), NH$_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl —CO—($C_1$-$C_6$)-alkyl, N($C_1$-$C_6$)-alkyl —COO—($C_1$-$C_6$)-alkyl, N($C_1$-$C_6$)-alkyl —CO-aryl, N($C_1$-$C_6$)-alkyl —CO-heterocycle, N($C_1$-$C_6$)-alkyl —COO-aryl, N($C_1$-$C_6$)-alkyl —COO-heterocycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—(CH$_2$)$_n$-aryl, O—(CH$_2$)$_n$-heterocycle, where n may be 0-6, where the aryl radical or heterocyclic radical may be substituted one to 3 times by F, Cl, Br, I, OH, CF$_3$, NO$_2$, CN, OCF$_3$, O—($C_1$-$C_6$)-alkyl, ($C_1$-$C_6$)-alkyl, NH$_2$, NH($C_1$-$C_6$)-alkyl, N(($C_1$-$C_6$)-alkyl)$_2$, SO$_2$—CH$_3$, COOH, COO—($C_1$-$C_6$)-alkyl, CONH$_2$.

Aryl means a phenyl, naphthyl-, biphenyl-, tetrahydronaphthyl-, alpha- or beta-tetralon-, indanyl- or indan-1-on-yl radical.

The aryl groups may be substituted one or more times by suitable groups such as, for example: F, Cl, Br, I, CF$_3$, NO$_2$, N$_3$, CN, COOH, COO($C_1$-$C_6$)alkyl, CONH$_2$, CONH($C_1$-$C_6$)alkyl, CON[($C_1$-$C_6$)alkyl]$_2$, cycloalkyl, (C—$C_{10}$)-alkyl, ($C_2$-$C_6$)-alkyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle; PO$_3$H$_2$, SO$_3$H, SO$_2$—NH$_2$, SO$_2$NH($C_1$-$C_6$)-alkyl, SO$_2$N[($C_1$-$C_6$)-alkyl]$_2$, S—($C_1$-$C_6$)-alkyl, S—(CH$_2$)$_n$-aryl, S—(CH$_2$)$_n$-heterocycle, SO—($C_1$-$C_6$)-alkyl, SO—(CH$_2$)$_n$-aryl, SO—(CH$_2$)$_n$-heterocycle, SO$_2$—($C_1$-$C_6$)-alkyl, SO$_2$—(CH$_2$)$_n$-aryl, SO$_2$—(CH$_2$)$_n$-heterocycle, SO$_2$—NH(CH$_2$)$_n$-aryl, SO$_2$—NH(CH$_2$)$_n$-heterocycle, SO$_2$—N($C_1$-$C_6$)-alkyl)(CH$_2$)$_n$-aryl, SO$_2$—N($C_1$-$C_6$)-alkyl)(CH$_2$)$_n$-heterocycle, SO$_2$—N((CH$_2$)$_n$-aryl)$_2$, SO$_2$—N((CH$_2$)$_n$-(heterocycle)$_2$ where n may be 0-6, and the aryl radical or heterocyclic radical may be substituted up to twice by F, Cl, Br, OH, CF$_3$, NO$_2$, CN, OCF$_3$, O—($C_1$-$C_6$)-alkyl, ($C_1$-$C_6$)-alkyl, NH$_2$; C(NH)(NH$_2$), NH$_2$, NH—($C_1$-$C_6$)-alkyl, N(($C_1$-$C_6$)-alkyl)$_2$, NH($C_1$-$C_7$)-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, N($C_1$-$C_6$)-alkyl —CO—($C_1$-$C_6$)-alkyl, N($C_1$-$C_6$)-alkyl —COO—($C_1$-$C_6$)-alkyl, N($C_1$-$C_6$)-alkyl —CO-aryl, N($C_1$-$C_6$)-alkyl —CO-heterocycle, N($C_1$-$C_6$)-alkyl —COO-aryl, N($C_1$-$C_6$)-alkyl —COO-heterocycle, N($C_1$-$C_6$)-alkyl —CO—NH—($C_1$-$C_6$)-alkyl), N($C_1$-$C_6$)-alkyl —CO—NH-aryl, N($C_1$-$C_6$)-alkyl —CO—NH-heterocycle, N(($C_1$-$C_6$)-alkyl)-CO—N—($C_1$-$C_6$)-alkyl)$_2$, N(($C_1$-$C_6$)-alkyl)-CO—N(($C_1$-$C_6$)-alkyl)-aryl, N(($C_1$-$C_6$)-alkyl)-CO—N(($C_1$-$C_6$)-alkyl)-heterocycle, N(($C_1$-$C_6$)-alkyl)-CO—N-(aryl)$_2$, N(($C_1$-$C_6$)-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6$)-alkyl)-aryl, N(heterocycle)-CO—N(($C_1$-$C_6$)-alkyl)-aryl, N(aryl)-CO—N-(aryl)$_2$, N(heterocycle)-CO—N-(aryl)$_2$, aryl, O—(CH$_2$)$_n$-aryl, O—(CH$_2$)$_n$-heterocycle, where n may be 0-6, where the aryl radical or heterocyclic radical may be substituted one to 3 times by F, Cl, Br, I, OH, CF$_3$, NO$_2$, CN, OCF$_3$, O—($C_1$-$C_6$)-alkyl, ($C_1$-$C_6$)-alkyl, NH$_2$, NH($C_1$-$C_6$)-alkyl, N(($C_1$-$C_6$)-alkyl)$_2$, SO$_2$—CH$_3$, COOH, COO—($C_1$-$C_6$)-alkyl, CONH$_2$.

Cycloalkyl means a ring system which comprises one or more rings, which is in saturated or partially unsaturated (with one or two double bonds) form and which is composed exclusively of carbon atoms, such as, for example, cyclopropyl, cyclopentyl, cyclopentenyl, cyclohexyl or adamantyl.

The cycloalkyl groups may be substituted one or more times by suitable groups such as, for example: F, Cl, Br, I, CF$_3$, NO$_2$, N$_3$, CN, COOH, COO($C_1$-$C_6$)alkyl, CONH$_2$, CONH($C_1$-$C_6$)alkyl, CON[($C_1$-$C_6$)alkyl]$_2$, cycloalkyl, ($C_1$-$C_{10}$)-alkyl, ($C_2$-$C_6$)-alkenyl, ($C_2$-$C_6$)-alkynyl, O—($C_1$-$C_6$)- alkyl O—CO—($C_1$-$C_6$)-alkyl, O—CO—($C_1$-$C_6$)-aryl, O—CO—($C_1$-$C_6$)-heterocycle;

$PO_3H_2$, $SO_3H$, $SO_2$—$NH_2$, $SO_2NH(C_1$-$C_6)$-alkyl, $SO_2N[(C_1$-$C_6)$-alkyl]$_2$, S—($C_1$-$C_6$)-alkyl, S—$(CH_2)_n$-aryl, S—$(CH_2)_n$-heterocycle, SO—($C_1$-$C_6$)-alkyl, SO—$(CH_2)_n$-aryl, SO—$(CH_2)_n$-heterocycle, $SO_2$—($C_1$-$C_6$)-alkyl, $SO_2$—$(CH_2)_n$-aryl, $SO_2$—$(CH_2)_n$-heterocycle, $SO_2$—$NH(CH_2)_n$-aryl, $SO_2$—$NH(CH_2)_n$-heterocycle, $SO_2$—$N(C_1$-$C_6)$-alkyl$(CH_2)_n$-aryl, $SO_2$—$N(C_1$-$C_6)$-alkyl$(CH_2)_n$-heterocycle, $SO_2$—$N((CH_2)_n$-aryl$)_2$, $SO_2$—$N((CH_2)_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$; $C(NH)(NH_2)$, $NH_2$, NH—($C_1$-$C_6$)-alkyl, $N((C_1$-$C_6)$-alkyl)$_2$, $NH(C_1$-$C_7)$-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, $N(C_1$-$C_6)$-alkyl —CO—($C_1$-$C_6$)-alkyl, $N(C_1$-$C_6)$-alkyl —COO—($C_1$-$C_6$)-alkyl, $N(C_1$-$C_6)$-alkyl —CO-aryl, $N(C_1$-$C_6)$-alkyl —CO-heterocycle, $N(C_1$-$C_6)$-alkyl —COO-aryl, $N(C_1$-$C_6)$-alkyl —COO-heterocycle, $N(C_1$-$C_6)$-alkyl —CO—NH—($C_1$-$C_6$)-alkyl), $N(C_1$-$C_6)$-alkyl —CO—NH-aryl, $N(C_1$-$C_6)$-alkyl —CO—NH-heterocycle, $N((C_1$-$C_6)$-alkyl)-CO—N—($C_1$-$C_6$)-alkyl)$_2$, $N((C_1$-$C_6)$-alkyl)-CO—N(($C_1$-$C_6)$-alkyl)-aryl, $N((C_1$-$C_6)$-alkyl)-CO—N(($C_1$-$C_6)$-alkyl)-heterocycle, $N((C_1$-$C_6)$-alkyl)-CO—N-(aryl)$_2$, $N((C_1$-$C_6)$-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6)$-alkyl)-aryl, N(heterocycle)-CO—N(($C_1$-$C_6)$-alkyl)-aryl, N(aryl)-CO—N-(aryl)$_2$, N(heterocycle)-CO—N-(aryl)$_2$, aryl, O—$(CH_2)_n$-aryl, O—$(CH_2)_n$-heterocycle, where n may be 0-6, where the aryl radical or heterocyclic radical may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SO_2$—$CH_3$, COOH, COO—($C_1$-$C_6$)-alkyl, $CONH_2$.

Heterocycle or heterocyclic means rings and ring systems which, apart from carbon, also comprise heteroatoms such as, for example, nitrogen, oxygen or sulfur. Also included in this definition are ring systems in which the heterocycle or the heterocyclic is fused to benzene nuclei. The heterocycle or heterocyclic group may be aromatic, saturated aliphatic or partly unsaturated aliphatic.

Suitable heterocycle groups are acridinyl, azocinyl, benzimidazolyl, benzofuryl, benzothienyl, benzothiophenyl, benzoxazolyl, benzthiazolyl, benztriazolyl, benztetrazolyl, benzisoxazolyl, benzisothiazolyl, benzimidazalinyl, carbazolyl, 4H-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2, 5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxanthiinyl, phenoxanzinyl, phthalazinyl, piperazinyl, piperidinyl, pteridinyl, purynyl, pyranyl, pyrazinyl, pyroazolidinyl, pyrazolinyl, pyrazolyl, pyridazinyl, pyridooxazoles, pyridoimidazoles, pyridothiazoles, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadazinyl, thiazolyl, 1,2,3-thiaeazolyl, 1,2,4-thiadiazolyl, 1,2,5-thiadiazolyl, 1,3,4-thiadiazolyl, thienyl, triazolyl, tetrazolyl and xanthenyl.

Pyridyl stands both for 2-, 3- and 4-pyridyl. Thienyl stands both for 2- and 3-thienyl. Furyl stands both for 2- and 3-furyl.

Also included are the corresponding N-oxides of these compounds, i.e., for example, 1-oxy-2-, 3- or 4-pyridyl.

Also included are derivatives of these heterocycles which are benzo-fused one or more times.

The heterocyclic rings or groups may be substituted one or more times by suitable groups such as, for example: F, Cl, Br, I, $CF_3$, $NO_2$, $N_3$, CN, COOH, COO($C_1$-$C_6$)alkyl, $CONH_2$, $CONH(C_1$-$C_6)$alkyl, $CON[(C_1$-$C_6)$alkyl]$_2$, cycloalkyl, ($C_1$-$C_{10}$)-alkyl, ($C_2$-$C_6$)-alkenyl, ($C_2$-$C_6$)-alkynyl, O—($C_1$-$C_6$)-alkyl O—CO—($C_1$-$C_6$)-alkyl, O—CO—($C_1$-$C_6$)-aryl, O—CO—($C_1$-$C_6$)-heterocycle;

$PO_3H_2$, $SO_3H$, $SO_2$—$NH_2$, $SO_2NH(C_1$-$C_6)$-alkyl, $SO_2N[(C_1$-$C_6)$-alkyl]$_2$, S—($C_1$-$C_6$)-alkyl, S—$(CH_2)_n$-aryl, S—$(CH_2)_n$-heterocycle, SO—($C_1$-$C_6$)-alkyl, SO—$(CH_2)_n$-aryl, SO—$(CH_2)_n$-heterocycle, $SO_2$—($C_1$-$C_6$)-alkyl, $SO_2$—$(CH_2)_n$-aryl, $SO_2$—$(CH_2)_n$-heterocycle, $SO_2$—$NH(CH_2)_n$-aryl, $SO_2$—$NH(CH_2)_n$-heterocycle, $SO_2$—$N(C_1$-$C_6)$-alkyl$(CH_2)_n$-aryl, $SO_2$—$N(C_1$-$C_6)$-alkyl$(CH_2)_n$-heterocycle, $SO_2$—$N((CH_2)_n$-aryl$)_2$, $SO_2$—$N((CH_2)_n$-(heterocycle)$_2$ where n may be 0-6, and the aryl radical or heterocyclic radical may be substituted up to twice by F, Cl, Br, OH, $CF_3$, $NO_2$, CN, $OCF_3$, O—($C_1$-$C_6$)-alkyl, ($C_1$-$C_6$)-alkyl, $NH_2$;

$C(NH)(NH_2)$, $NH_2$, NH—($C_1$-$C_6$)-alkyl, $N((C_1$-$C_6)$-alkyl)$_2$, $NH(C_1$-$C_7)$-acyl, NH—CO—($C_1$-$C_6$)-alkyl, NH—COO—($C_1$-$C_6$)-alkyl, NH—CO-aryl, NH—CO-heterocycle, NH—COO-aryl, NH—COO-heterocycle, NH—CO—NH—($C_1$-$C_6$)-alkyl, NH—CO—NH-aryl, NH—CO—NH-heterocycle, $N(C_1$-$C_6)$-alkyl —CO—($C_1$-$C_6$)-alkyl, $N(C_1$-$C_6)$-alkyl —COO—($C_1$-$C_6$)-alkyl, $N(C_1$-$C_6)$-alkyl —CO-aryl, $N(C_1$-$C_6)$-alkyl —CO-heterocycle, $N(C_1$-$C_6)$-alkyl —COO-aryl, $N(C_1$-$C_6)$-alkyl COO-heterocycle, $N(C_1$-$C_6)$-alkyl —CO—NH—($C_1$-$C_6$)-alkyl), $N(C_1$-$C_6)$-alkyl —CO—NH-aryl, $N(C_1$-$C_6)$-alkyl —CO—NH-heterocycle, $N((C_1$-$C_6)$-alkyl)-CO—N—($C_1$-$C_6$)-alkyl)$_2$, $N((C_1$-$C_6)$-alkyl)-CO—N(($C_1$-$C_6)$-alkyl)-aryl, $N((C_1$-$C_6)$-alkyl)-CO—N(($C_1$-$C_6)$-alkyl)-heterocycle, $N((C_1$-$C_6)$-alkyl)-CO—N-(aryl)$_2$, $N((C_1$-$C_6)$-alkyl)-CO—N-(heterocycle)$_2$, N(aryl)-CO—($C_1$-$C_6$)-alkyl, N(heterocycle)-CO—($C_1$-$C_6$)-alkyl, N(aryl)-COO—($C_1$-$C_6$)-alkyl, N(heterocycle)-COO—($C_1$-$C_6$)-alkyl, N(aryl)-CO-aryl, N(heterocycle)-CO-aryl, N(aryl)-COO-aryl, N(heterocycle)-COO-aryl, N(aryl)-CO—NH—($C_1$-$C_6$)-alkyl), N(heterocycle)-CO—NH—($C_1$-$C_6$)-alkyl), N(aryl)-CO—NH-aryl, N(heterocycle)-CO—NH-aryl, N(aryl)-CO—N—($C_1$-$C_6$)-alkyl)$_2$, N(heterocycle)-CO—N—($C_1$-$C_6$)-alkyl)$_2$, N(aryl)-CO—N(($C_1$-$C_6)$-alkyl)-aryl, N(heterocycle)-CO—N(($C_1$-$C_6)$-alkyl)-aryl, N(aryl)-CO—N-(aryl)$_2$, N(heterocycle)-CO—N-(aryl)$_2$, aryl, O—$(CH_2)_n$-aryl, O—$(CH_2)_n$-heterocycle, where n may be 0-6, where the aryl radical or heterocyclic radical may be substituted one to 3 times by F, Cl, Br, I, OH, $CF_3$, $NO_2$, CN, $OCF_3$, O—($C_1$-$C_6$)-alkyl, ($C_1$-$C_6$)-alkyl, $NH_2$, $NH(C_1$-$C_6)$-alkyl, $N((C_1$-$C_6)$-alkyl)$_2$, $SO_2$—$CH_3$, COOH, COO—($C_1$-$C_6$)-alkyl, $CONH_2$.

The compound(s) of the formula (I) may also be administered in combination with additional active ingredients.

The amount of a compound of formula I necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg and 50 mg) per day and per kilogram of bodyweight, for example 3-10 mg/kg/day. An intravenous dose may be, for example, in the range from 0.3 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter (ml.). Single doses may contain, for example, from 1 mg to 10 g of the active ingredient. Thus, ampoules for injections may contain, for example, from 1 mg to 100 mg, and single-dose formulations which can be administered orally, such as, for example, capsules or tablets, may contain, for example, from 1.0 to 1000 mg, typically from 10 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, slow-dissolving, oral tablets, each of which contain a defined amount of the compound of formula I; as powders or granules, as solution or suspension in an aqueous or non-aqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise slow-dissolving, oral tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa buffer, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

Other additional active ingredients suitable for combination products are: all antidiabetic agents mentioned in the Rote Liste 2004, chapter 12 which is incorporated herein by reference. They may be combined with the compounds of the formula I of the invention, in particular for a synergistic improvement of the effect. Administration of the active ingredient combination may take place either by separate administration of the active ingredients to the patient or in the form of combination products in which a plurality of active ingredients are present in one pharmaceutical preparation. Most of the active ingredients listed below are disclosed in the USP Dictionary of USAN and International Drug Names, US Pharmacopeia, Rockville 2001 which is also incorporated herein by reference.

Antidiabetics include insulin and insulin derivatives such as, for example, Lantus® (see www.lantus.com) or HMR 1964, fast-acting insulins, i.e., see U.S. Pat. No. 6,221,633 to Ertle et. al., GLP-1 derivatives such as, for example, those disclosed in WO 98/08871 by Novo Nordisk A/S and orally effective hypoglycemic active ingredients.

The orally effective hypoglycemic active ingredients include, preferably, sulfonylureas, biguanidines, meglitinides, oxadiazolidinediones, thiazolidinediones, glucosidase inhibitors, glucagon antagonists, GLP-1 agonists, potassium channel openers such as, for example, those disclosed in WO 97/26265 and WO 99/03861 of Novo Nordisk A/S, insulin sensitizers, inhibitors of liver enzymes involved in the stimulation of gluconeogenesis and/or glycogenolysis, modulators of glucose uptake, compounds which alter lipid metabolism, such as anti-hyperlipidemic active ingredients and anti-lipidemic active ingredients, compounds which reduce food intake, peroxisome proliferator activated receptor (PPAR) and PXR agonists and active ingredients which act on the ATP-dependent potassium channel of the beta cells.

In one embodiment of the invention, the compounds of the formula I are administered in combination with an HMGCoA reductase inhibitor such as simvastatin, fluvastatin, pravastatin, lovastatin, atorvastatin, cerivastatin, rosuvastatin.

In one embodiment of the invention, the compounds of the formula I are administered in combination with a cholesterol absorption inhibitor such as, for example, ezetimibe, tiqueside, pamaqueside or with a compound as described in PCT/EP 2004/00269, PCT/EP 2003/05815, PCT/EP 2003/05814, PCT/EP 2003/05816, EP 0114531, U.S. Pat. No. 6,498,156.

In one embodiment of the invention, the compounds of the formula I are administered in combination with a PPAR gamma agonist, such as, for example, rosiglitazone, pioglitazone, JTT-501, GI 262570.

In one embodiment of the invention, the compounds of the formula I are administered in combination with a PPAR alpha agonist, such as, for example, GW 9578, GW 7647.

In one embodiment of the invention, the compounds of the formula I are administered in combination with a mixed PPAR alpha/gamma agonist, such as, for example, GW 1536, AVE 8042, AVE 8134, AVE 0847, or as described in PCT/US 11833, PCT/US 11490, DE10142734.4.

In one embodiment of the invention, the compounds of the formula I are administered in combination with a fibrate such as, for example, fenofibrate, clofibrate, bezafibrate.

In one embodiment of the invention, the compounds of the formula I are administered in combination with an MTP inhibitor such as, for example, implitapide, BMS-201038, R-103757.

In one embodiment of the invention, the compounds of the formula I are administered in combination with bile acid absorption inhibitor; see, for example, U.S. Pat. No. 6,245,744 or U.S. Pat. No. 6,221,897 to Frick et. al. al., such as, for example, HMR 1741.

In one embodiment of the invention, the compounds of the formula I are administered in combination with a CETP inhibitor, such as, for example, JTT-705.

In one embodiment of the invention, the compounds of the formula I are administered in combination with a polymeric bile acid adsorbent such as, for example, cholestyramine, colesevelam.

In one embodiment of the invention, the compounds of the formula I are administered in combination with an LDL receptor inducer; see U.S. Pat. No. 6,342,512 to Kirsch et. al. such as, for example, HMR1171, HMR1586.

In one embodiment of the invention, the compounds of the formula I are administered in combination with an ACAT inhibitor, such as, for example, avasimibe.

In one embodiment of the invention, the compounds of the formula I are administered in combination with an antioxidant, such as, for example, OPC-14117.

In one embodiment of the invention, the compounds of the formula I are administered in combination with a lipoprotein lipase inhibitor, such as, for example, NO-1886.

In one embodiment of the invention, the compounds of the formula I are administered in combination with an ATP-citrate lyase inhibitor, such as, for example, SB-204990.

In one embodiment of the invention, the compounds of the formula I are administered in combination with a squalene synthetase inhibitor, such as, for example, BMS-188494.

In one embodiment of the invention, the compounds of the formula I are administered in combination with a lipoprotein (a) antagonist, such as, for example, CI-1027 or nicotinic acid.

In one embodiment of the invention, the compounds of the formula I are administered in combination with a lipase inhibitor, such as, for example, orlistat.

In one embodiment of the invention, the compounds of the formula I are administered in combination with insulin.

In one embodiment, the compounds of the formula I are administered in combination with a sulfonylurea such as, for example, tolbutamide, glibenclamide, glipizide or glimepiride.

In one embodiment, the compounds of the formula I are administered in combination with a biguanide, such as, for example, metaformin.

In one further embodiment, the compounds of the formula I are administered in combination with a meglitinide, such as, for example, repaglinide.

In one embodiment, the compounds of the formula I are administered in combination with a thiazolidinedione, such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl] methyl]-2,4-thiazolidinedione.

In one embodiment, the compounds of the formula I are administered in combination with an α-glucosidase inhibitor, such as, for example, miglitol or acarbose.

In one embodiment, the compounds of the formula I are administered in combination with an adenosine A1 agonist such as, for example, those described in EP 0912520 or PCT/EP06749.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with more than one of the aforementioned compounds, e.g. in combination with a sulfonylurea and metaphoric, with a sulfonylurea and acarbose, repaglinide and metaformin, insulin and a sulfonylurea, insulin and metaformin, insulin and troglitazone, insulin and lovastatin, etc.

In a further embodiment, the compounds of the formula I are administered in combination with CART modulators (see "Cocaine-Amphetamine-Regulated Transcript Influences Energy Metabolism, Anxiety and Gastric Emptying in Mice" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)methyl] cyclohexylmethyl}amide, hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6, 7-hexahydropyrazolo[4,3-c]pyridin-5-yl)-1-(4-chlorophenyl)-2-oxoethyl]amide; (WO 01/91752)), orexin antagonists (e.g. 1-(2-methylbenzoxazol-6-yl)-3-[1,5]naphthyridin-4- ylurea hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]ethanol hydrochloride (WO 01/83451)), CB1 (cannabinoid receptor 1) receptor antagonists (e.g. rimonabant or the active ingredients mentioned in WO 02/28346), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed serotonergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the other active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the other active ingredient is dexamphetamine or amphetamine.

In one embodiment, the other active ingredient is fenfluramine or dexfenfluramine.

In another embodiment, the other active ingredient is sibutramine.

In one embodiment, the other active ingredient is orlistat.

In one embodiment, the other active ingredient is mazindol or phentermine.

In one embodiment, the other active ingredient is rimonabant.

In one embodiment, the compounds of the formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6.) Caromax® is a carob-containing product from Nutrinova, Nutrition Specialties & Food Ingredients GmbH, Industriepark Hochst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

It will be appreciated that every suitable combination of the compounds of the invention with one or more of the aforementioned compounds and optionally one or more other pharmacologically active substances is regarded as falling within the protection conferred by the present invention. The examples detailed below are provided to better describe and more specifically set forth the compounds, processes and methods of this invention. It is to be recognized that they are for illustrative purposes only however, and should not be interpreted as limiting the spirit and scope of the invention as later recited by the claims that follow.

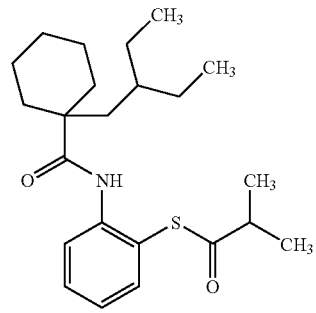

JTT-705

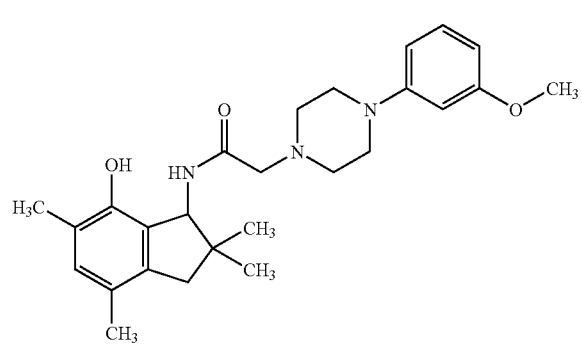

OPC-14117

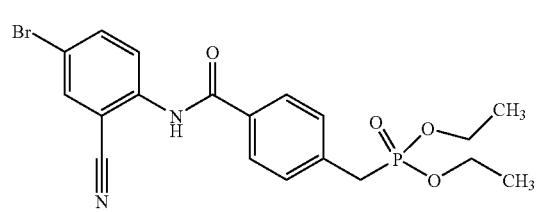

NO-1886

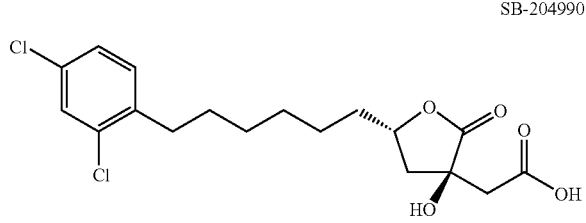

SB-204990

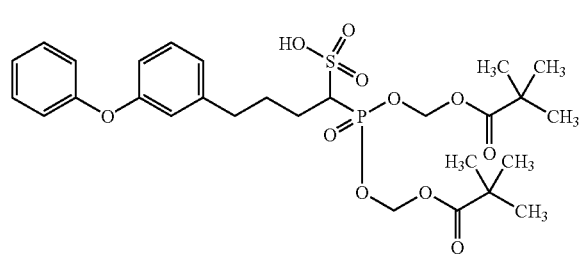

BMS-188494

-continued

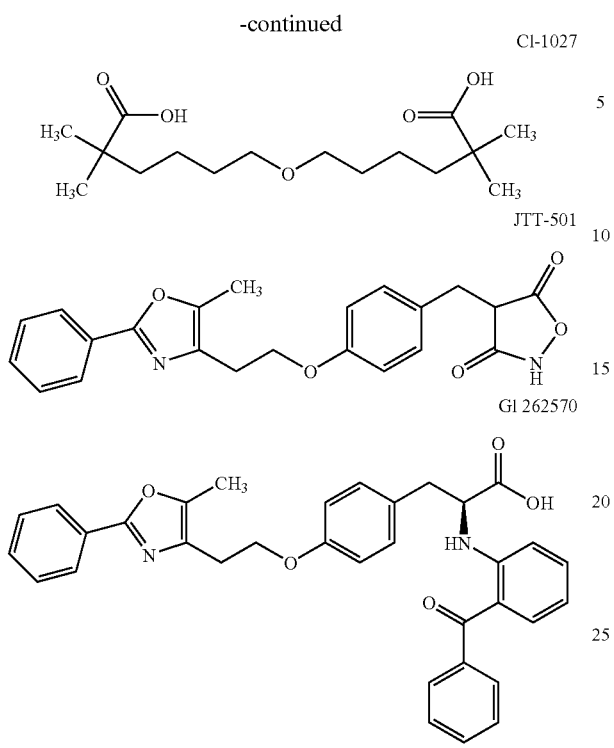

Cl-1027

JTT-501

Gl 262570

EXAMPLES

Background

The compounds of formula I of the present invention can be prepared by reacting suitable starting materials of the formula II in which X is a leaving group such as chlorine, bromine, iodine, sulfonyloxy, sulfinyl, sulfoxyl with a compound of the formula IV, where appropriate in the presence of suitable bases and in suitable solvents.

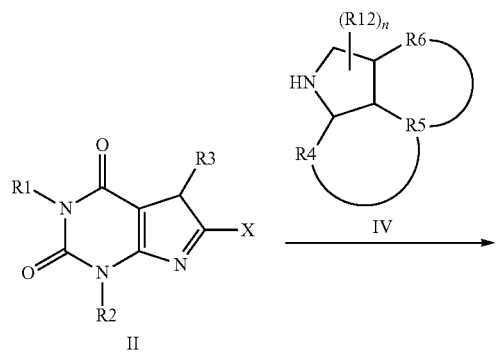

-continued

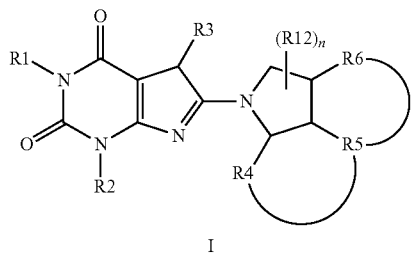

I

In the cases where R11 is hydrogen, it may be expedient to employ the residue IV in a form protected on the nitrogen function, and to eliminate the protective group again after reaction with 11 has taken place. Such suitable protective groups and methods for introduction and elimination are known see:Theodora W. Greene and Peter G. M. Wuts, Protective Groups in Organic Synthesis, 3rd Edition, John Wiley & Sons, Inc., New York, 1999 which is also incorporated herein by reference.

The halogen compounds of the formula II can be obtained by known methods such as, for example, by halogenation of the corresponding H or hydroxy compound (formula II, X=H). Suitable halogenating agents may be by way of example halogens such as chlorine and bromine, N-bromosuccinimide, phosphorus pentachloride or phosphorus oxychloride.

Synthesis of compounds of the formula II is described in the literature (see Houben Weyl E9b/2, pp. 331 et seq. and literature cited therein all of which are incorporated herein by reference. They can be obtained for example starting from diaminopyrimidine derivatives or aminoimidazole carboxamides by reaction with suitable reagents and be converted by targeted chemical modifications such as hydrolysis, alkylation, halogenation or acylation into the desired starting compounds of the formula II. The radicals R1 to R3 can be prepared by methods known per se by alkylating appropriate known precursors, it being possible to vary the sequence. However, they can also be introduced through appropriate selection of suitable precursors in the preparation of the xanthine structure.

The bicyclic amines IV can be synthesized by methods known from the literature. Thus, the preparation of various derivatives of this class of substances, such as, for example, of octahydropyrrolo[3,4-b]pyrrole and 1-methyloctahydropyrrolo[3,4-b]pyrrole has been described in EP 0 393 424.

Some derivatives of the formula IV, such as, for example, octahydropyrrolo[3,4-b]pyridine or octahydropyrrolo[3,4-c]pyridine, are commercially available.

TABLE 1

I

| Ex. | R1 | R2 | R3 | R4-R5 | R5-R6 | n (R12) |
|---|---|---|---|---|---|---|
| 1 | —CH$_2$—CO-Phenyl | —CH$_3$ | —CH$_2$—CH=C—(CH$_3$)$_2$ | —CH$_2$—NH—CH$_2$— | R6 = H racemate | 0 |
| 1a | —CH$_2$—CO-Phenyl | —CH$_3$ | —CH$_2$—CH=C—(CH$_3$)$_2$ | —CH$_2$—NH—CH$_2$—•HCl | R6 = H diastereomer 1 | 0 |
| 1b | —CH$_2$—CO-Phenyl | —CH$_3$ | —CH$_2$—CH=C—(CH$_3$)$_2$ | —CH$_2$—NH—CH$_2$—•HCl | R6 = H diastereomer 2 | 0 |
| 2 | —CH$_2$—CO-Phenyl | —CH$_3$ | —CH$_2$—CH=C—(CH$_3$)$_2$ | —CH$_2$—N(CH$_3$)—CH$_2$— | R6 = H | 0 |
| 3 | —CH$_2$—CO-Phenyl | —CH$_3$ | —CH$_2$—CH=C—(CH$_3$)$_2$ | R4 = H | NH—CH$_2$—CH$_2$—CH$_2$ | 0 |
| 4 | —CH$_2$—CO-Phenyl | —CH$_3$ | —CH$_2$—CH=C—(CH$_3$)$_2$ | R4 = H | —NH—CH$_2$—CH$_2$—CH$_2$ | 0 |
| 5 | —CH$_2$—CO-Phenyl | —CH$_3$ | —CH$_2$-Ph | —CH$_2$—NH—CH$_2$—•HCl | R6 = H | 0 |
| 6 | F$_3$C—CH$_2$— | —CH$_3$ | —CH$_2$-Ph | —CH$_2$—NH—CH$_2$—•HCl | R6 = H | 0 |
| 7 | 5-Methylisoxazol-3-ylmethyl | —CH$_3$ | —CH$_2$-Ph | —CH$_2$—NH—CH$_2$—•HCl | R6 = H | 0 |
| 8 | —CH$_2$—CH=C—(CH$_3$)$_2$ | —CH$_3$ | —CH-Ph | —CH$_2$—NH—CH$_2$—•HCl | R6 = H | 0 |
| 9 | —CH$_2$—CO-Phenyl | —CH$_3$ | —CH$_2$,CH$_2$—CF$_3$ | —CH$_2$—NH—CH$_2$—•HCl | R6 = H | 0 |
| 10 | —CH$_2$-Ph-4-F | —CH$_3$ | —CH$_2$,CH$_2$—CF$_3$ | —CH$_2$—NH—CH$_2$—•HCl | R6 = H | 0 |
| 11 | Cyclohexylmethyl | —CH$_3$ | —CH$_2$,CH$_2$—CF$_3$ | —CH$_2$—NH—CH$_2$—•HCl | R6 = H | 0 |
| 12 | —CH$_2$—CH=CH-Ph-4-Cl | —CH$_3$ | —CH$_2$,CH$_2$—CF$_3$ | —CH$_2$—NH—CH$_2$—•HCl | R6 = H | 0 |
| 13 | —CH$_2$,CH$_2$—CF3 | —CH$_3$ | —CHOH-Ph | —CH$_2$—NH—CH$_2$—•HCl | R6 = H | 0 |
| 14 | —CH$_2$—CO-Phenyl | —CH$_3$ | —CH$_2$—CH=C—(CH$_3$)$_2$ | —CH$_2$—NH—CH$_2$—•HCl | R6 = H | 0 |
| 15 | 5-Fluorobenzothiazol-2-ylmethyl | —CH$_2$—CH$_3$ | —CH$_3$ | —CH$_2$—NH—CH$_2$—•HCl | R6 = H | 0 |
| 16 | 5-Cyclopropyl-[1,3,4]thiadiazol-2-ylmethyl] | —CH$_3$ | —CH$_3$ | —CH$_2$—CH—C—(CH$_3$)$_2$ | R6 = H | 0 |
| 17 | —CH$_3$ | —CH$_3$ | —CH$_2$—CH=C—(CH$_3$)$_2$ | —CH$_2$—NH—CH$_2$—•HCl | R6 = H | 0 |
| 18 | —CH$_3$ | Cyclopropyl | —CH$_2$—CH=C—(CH$_3$)$_2$ | —CH$_2$—NH—CH$_2$—•HCl | R6 = H | 0 |
| 19 | —CH$_3$ | Cyclopropyl | —CH$_2$-(Ph-2-Cl-4-F) | —CH$_2$—NH—CH$_2$—•HCl | R6 = H | 0 |
| 20 | —CH$_2$—CO-Phenyl | —CH$_3$ | —CH$_2$—CC—CH$_3$ | —CH$_2$—NH—CH$_2$—•HCl | R6 = H | 0 |
| 21 | —CH$_2$-Ph | —CH$_3$ | —CH$_2$—CH=C—(CH$_3$)$_2$ | —CH$_2$—NH—CH$_2$—•HCl | R6 = H | 0 |
| 22 | —CH$_3$ | —CH$_3$ | —CH$_2$—CH=C—(CH$_3$)$_2$ | —CH$_2$—NH—CH$_2$—•HCl | R6 = H | 0 |
| 23 | —CH$_2$—CO-Phenyl | —CH$_3$ | —CH$_2$—CH=C—(CH$_3$)$_2$ | —CH$_2$—NH—CH$_2$—•HCl | R6 = H | 0 |
| 24 | —CH$_2$—CF$_2$-Ph-4Br | —CH$_3$ | —CH$_2$—CH=C—(CH$_3$)$_2$ | —CH$_2$—NH—CH$_2$—•CF$_3$COOH | R6 = H Diastereomer 1 | 0 |
| 25 | —CH$_2$—CF$_2$-Ph-4Br | —CH$_3$ | —CH$_2$—CH=C—(CH$_3$)$_2$ | —CH$_2$—NH—CH$_2$—•CF$_3$COOH | R6 = H Diastereomer 2 | 0 |
| 26 | —CH$_2$—CF$_2$-Ph-4F | —CH$_3$ | —CH$_2$—CH=C—(CH$_3$)$_2$ | —CH$_2$—NH—CH$_2$—•CF$_3$COOH | R6 = H Diastereomer 1 | 0 |
| 27 | —CH$_2$—CF$_2$-Ph-4Fr | —CH$_3$ | —CH$_2$—CH=C—(CH$_3$)$_2$ | —CH$_2$—NH—CH$_2$—•CF$_3$COOH | R6 = H Diastereomer 2 | 0 |
| 28 | 3-hydroxy-3-methyl-butyl | —CH$_2$—CH$_3$ | —CH$_2$—CH=C—(CH$_3$)$_2$ | —CH$_2$—NH—CH$_2$—•HCl | R6 = H | 0 |
| 29 | tBu-CO—CH$_2$— | —CH$_3$ | —CH$_2$—CC—CH$_3$ | —CH$_2$—NH—CH$_2$—•HCl | R6 = H | 0 |
| 30 | —CH$_3$ | —CH$_3$ | —CH$_2$—CO-Phenyl | —CH$_3$—NH—CH$_2$—•HCl | R6 = H | 0 |

The following theoretical examples serve to illustrate the invention further:

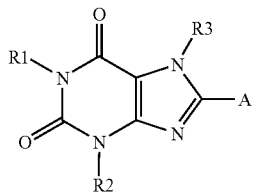

| Theoretical example | A | R1 | R2 | R3 |
|---|---|---|---|---|
| A | A3 | $CH_3$ | $CH_2CH_3$ | $CH_2CH_2CH_2CH_3$ |
| B | A4 | $CH_2CH_2(C_6H_5)$ | Cyclopropyl | $CH_2CH_2-(C_6H_4)$-2-$CH_3$ |
| C | A1 | $CH_2-CO-(C_6H_4)$-4-$CF3$ | $CH_3$ | $CH_2CH=CHCH_3$ |
| D | A4 | $CH_2-CO-(C_6H_4)$-3-$OCF3$ | $CH_2CH_2N(CH_3)_2$ | $CH_2C\equiv CCH_3$ |
| E | A5 | $CH_2-CHOH-(C_6H_4)$-2-$NHCOCH3$ | $CH_3$ | $CH_2CH=C(CH_3)_2$ |
| F | A2 | $CH_2-CF_2-(C_6H_5)$ | $CH_3$ | $CH_2(C_6H_5)$-2-CN |
| G | A6 | $CH_2CO(C_6H_5)$ | $CH_2CH(CH_3)_2$ | $CH_2CH_2(C_6H_4)$-4-F |
| H | A1 | $CH_2(C_6H_4)$-4-F | $CH_3$ | $CH_2$-Pyrid-3-yl |
| I | A3 | $CH_2$-Isoquinolin-1-yl | Cyclopentyl | $CH_2CH_2CF_3$ |
| J | A1 | $CH_2-CONH$-Pyridy-2-yl | Cyclopropyl | $CH_2CH_2CH(CH_3)_2$ |
| K | A3 | $CH_2COPh$-3-F | $CH_2CF_3$ | $CH_2$-Ph-2-Cl |
| L | A2 | $CH_2CF_2Ph$ | $CH_3$ | $CH_2$-Cyclohexyl |

The compounds of the formula I are notable for beneficial effects on lipid and carbohydrate metabolism, in particular they lower the blood glucose level and are suitable for the treatment of type 2 diabetes, of insulin resistance, of dyslipidemias and of metabolic syndrome/syndrome X. The compounds are also suitable for the prophylaxis and treatment of arteriosclerotic manifestations. The compounds can be employed alone or in combination with other blood glucose-lowering active ingredients. The compounds act as dipeptidyl peptidase IV (DPP-IV) inhibitors and are also suitable for the treatment of disorders of wellbeing and other psychiatric indications such as, for example, depressions, anxiety states, anxiety neuroses, schizophrenia and for the treatment of disorders associated with the circadian rhythm, for weight reduction in mammals, for the treatment of immunological disorders, and for the treatment of drug abuse.

They are also suitable for the treatment of cancer, arthritis, osteoarthritis, osteoporosis, sleep disorders, sleep apnea, female and male sexual disorders, inflammations, acne, pigmentation of the skin, disorders of steroid metabolism, skin diseases, psoriasis, mycoses, neurodegenerative diseases, multiple sclerosis and Alzheimer's disease.

The activity of the compounds was assayed as follows:
Measurement of the DPP-IV activity:
Material:
DPP-IV from porcine kidney (Sigma, Munich)
H-Ala-Pro-AFC (Bachem, Weil am Rhein)
Assay conditions:
DPP-IV (1 mU/ml, final concentration)
H-Ala-Pro-AFC (15 µM, final concentration)
in Tris/HCl (40 mM, pH 7.4), total volume 0.2 ml The reaction was carried out at room temperature for various times (typically 10 min) and stopped at the end of the reaction by adding 20 µl of $ZnCl_2$(1 M). The H-Ala-Pro-AFC conversion was determined fluorimetrically by measuring the emission at 535 nm after excitation at 405 nm. When inhibitors were added, the added buffer volume was adapted so that a total volume of 200 µl was maintained for the assay mixture.

$IC_{50}$ values for inhibitors were determined by varying the inhibitor concentrations with the stated substrate concentration of 15 µM. Ki and Km values were found by appropriate variation of substrate concentration and inhibitor concentration as described (Dixon, M. and Webb, E. C. (1979) Enzymes, third edition, pp. 47-206, Academic Press). The values for Km, IC50 and Ki were calculated using a commercially available software package (Leatherbarrow, R. J. (1992) GraFit Version 3.0, Erithacus Software Ltd. Staines, U.K.).

TABLE 2

Biological activity of exemplary embodiments:

| Exemplary embodiment No. | IC-50 (nM) |
|---|---|
| 1 | 1.6 |
| 1a | 1 |
| 1b | 6.7 |
| 3 | 51 |
| 4 | 17 |
| 5 | 7.2 |
| 14 | 12 |
| 15 | 5 |
| 16 | 19 |
| 21 | 71 |
| 35 | 50 |
| 41 | 10.5 |
| 42 | 10 |
| 97 | 20 |

It can be inferred from the table that the compounds of the formula I inhibit the activity of DPP-IV (dipeptidyl peptidase IV) and are thus very suitable for lowering the blood of some exemplary embodiments is described in detail below, and the glucose level.

The preparation of some exemplary embodiments is described in detail below, and the other compounds of the formula I were obtained analogously:

Example 1

8-(cis-Hexahydropyrrolo[3,4-b]pyrrol-1-yl)-3-methyl-7-(3-methylbut-2-enyl)-1-(2-oxo-2-phenylethyl)-3,7-dihydropurin-2,6-dione hydrochloride 1.1 tert-Butyl 1-[3-methyl-7-(3-methylbut-2-enyl)-2,6-dioxo-1-(2-oxo-2-phenylethyl)-2,3,6,7-tetrahydro-1H-purin-8-yl]-cis-hexahydropyrrolo[3,4-b]pyrrole-5-carboxylate 100 mg of potassium carbonate and 105 mg of tert-butyl cis-hexahydropyrrolo[3,4b]pyrrole-5-carboxylate were added to a solution of 150 mg of 8-bromo-3-methyl-7-(3-methylbut-2-enyl)-1-(2-oxo-2-phenylethyl)-3,7-dihydropurine-2,6-dione in 1.5 ml of NMP, and the mixture was heated at 90° C. with stirring for 6 hours. The mixture was cooled and then 20 ml of water and a few drops of glacial acetic acid were added, and the precipitate was stirred at room temperature and then filtered off with suction and dried in vacuum.

Yield: 140 mg m.p.: 156° C.

1.2b) 8-(cis-Hexahydropyrrolo[3,4-b]pyrrol-1-yl)-3-methyl-7-(3-methylbut-2-enyl)-1-(2-oxo-2-phenylethyl)-3,7-dihydropurine-2,6-dione hydrochloride 60 mg of tert-butyl 1-[3-methyl-7-(3-methylbut-2-enyl)-2,6-dioxo-1-(2-oxo-2-phenylethyl)-2,3,6,7-tetrahydro-1H-purin-8-yl]-cis-hexahydropyrrolo[3,4-b]pyrrole-5-carboxylate were dissolved in 5 ml of ethyl acetate, 1 ml of a saturated hydrogen chloride solution in ethyl acetate was added, and the mixture was stirred at room temperature overnight.

The amorphous precipitate was filtered off with suction and dried in vacuum.

Yield: 33 mg m.p.: resin MS: M+1=463

Example 1a 8-(Hexahydropyrrolo[3,4-b]pyrrol-1-yl)-3-methyl-7-(3-methylbut-2-enyl)-1-(2-oxo-2-phenyl-ethyl)-3,7-dihydropurine-2,6-dione hydrochloride (diastereomer 1) MS: M+1=463

This compound was obtained as faster-eluting isomer by separation of tert-butyl 1-[3-methyl-7-(3-methylbut-2-enyl)-2,6-dioxo-1-(2-oxo-2-phenylethyl)-2,3,6,7-tetrahydro-1H-purin-8-yl]-cis-hexahydropyrrolo[3,4-b]pyrrole-5-carboxylate on a chiral column (Chiralpak AD 10×40 cm, manufactured by Merck; eluent: methanol+0.1% diethylamine; flow rate:200 ml/min) and was isolated as amorphous hydrochloride by dissolving in ethyl acetate and precipitating with HCl.

Example 1b 8-(Hexahydropyrrolo[3,4-b]pyrrol-1-yl)-3-methyl-7-(3-methylbut-2-enyl)-1-(2-oxo-2-phenyl-ethyl)-3,7-dihydropurine-2,6-dione hydrochloride (diastereomer 2) MS: M+1=463

This compound was obtained as slower-eluting isomer by separation of tert-butyl 1-[3-methyl-7-(3-methylbut-2-enyl)-2,6-dioxo-1-(2-oxo-2-phenylethyl)-2,3,6,7-tetrahydro-1H-purin-8-yl]-cis-hexahydropyrrolo[3,4-b]pyrrole-5-carboxylate on a chiral column (Chiralpak AD 10×40 cm, manufactured by Merck; eluent: methanol+0.1% diethylamine; flow rate:200 ml/min) and was isolated as amorphous hydrochloride by dissolving in ethyl acetate and precipitating with HCl.

Example 2

3-Methyl-7-(3-methylbut-2-enyl)-8-(cis-5-methyl-hexahydropyrrolo[3,4-b]pyrrole-1-yl)-1-(2-oxo-2-phenylethyl)-3,7-dihydropurine-2,6-dione 100 mg of potassium carbonate and 55 g of cis-5-methyloctahydropyrrolo[3,4-b]pyrrole are added to a solution of 150 mg of 8-bromo3-methyl-7-(3-methylbut-2-enyl)-1-(2-oxo-2-phenylethyl)-3,7-dihydropurine-2,6-dione in 1.5 ml of NMP, and the mixture was heated at 90° C. with stirring for 3 hours. The mixture was cooled and then 20 ml of water were added, and the precipitate was filtered off after stirring at room temperature and dried in vacuum.

Yield: 115 mg m.p.:73.5° C. MS: M+1=477

Example 3

3-Methyl-7-(3-methyl but-2-enyl)-8-(cis-octahydropyrrolo[3,4-b]pyridin-6-yl)-1-(2-oxo-2-phenylethyl)-3,7-dihydropurine-2,6-dione 32 mg of potassium carbonate and 18 mg of cis-octahydropyrrolo[3,4-b]pyridine were added to a solution of 50 mg of 8-bromo-3-methyl-7-(3-methylbut-2-enyl)-1-(2-oxo-2-phenylethyl)-3,7-dihydropurine-2,6-dione in 1.5 ml of DMF, and the mixture was heated at 80° C. with stirring for 3 hours. The mixture was cooled and then concentrated, and the residue was taken up in 20 ml of water and extracted with 20 ml of ethyl acetate. The organic phase was dried over sodium sulfate and evaporated in vacuo. The oily residue was purified by column chromatography (silica gel, mobile phase: methylene chloride. methanol=95:5).

Yield: 35 mg m.p.: resin MS: M+1=477

Example 4

8-(cis-Hexahydropyrrolo[3,4-b]pyrrol-5-yl)-3-methyl-7-(3-methylbut-2-enyl)-1-(2-oxo-2-phenylethyl)-3,7-dihydropurine-2,6-dione was obtained in analogy to Example 5 starting from cis-octahydropyrrolo[3,4-b]pyrrole.

M.p. resin MS: M+1=463

The following examples were prepared in a similar manner:

Example 5

7-Benzyl-8-(hexahydropyrrolo[3,4-b]pyrrol-1-yl)-3-methyl-1-(2-oxo-2-phenylethyl)-3,7-dihydropurine-2,6-dione hydrochloride MS: M+1=485

Example 6

7-Benzyl-8-(hexahydropyrrolo[3,4-b]pyrrol-1-yl)-3-methyl-1-(2,2,2-trifluoroethyl)-3,7-dihydropurine-2,6-dione hydrochloride MS: M+1=449

Example 7

7-Benzyl-8-(hexahydropyrrolo[3,4-b]pyrrol-1-yl)-3-methyl-1-(5-methylisoxazol-3-ylmethyl)-3,7-dihydropurine-2,6-dione hydrochloride MS: M+1=462

Example 8

7-Benzyl-8-(hexahydropyrrolo[3,4-b]pyrrol-1-yl)-3-methyl-1-(3-methylbut-2-enyl)-3,7-dihydropurine-2,6-dione hydrochloride MS: M+1=435

Example 9

8-(Hexahydropyrrolo[3,4-b]pyrrol-1-yl)-3-methyl-1-(2-oxo-2-phenylethyl)-7-(3,3,3-trifluoropropyl)-3,7-dihydropurine-2,6-dione hydrochloride MS: M+1=491

Example 10

1-(4-Fluorobenzyl)-8-(hexahydropyrrolo[3,4-b]pyrrol-1-yl)-3-methyl-7-(3,3,3-trifluoropropyl)-3,7-dihydropurine-2,6-dione hydrochloride MS: M+1=481

Example 11

1-Cyclohexylmethyl-8-(hexahydropyrrolo[3,4-b]pyrrol-1-yl)-3-methyl-7-(3,3,3-trifluoro-propyl)-3,7-dihydropurine-2,6-dione hydrochloride MS: M+1=469

Example 12

1-[3-(4-Chlorophenyl)allyl]-8-(hexahydropyrrolo[3,4-b]pyrrol-1-yl)-3-methyl-7-(3,3,3-trifluoropropyl)-3,7-dihydropurine-2,6-dione hydrochloride MS: M+1=523

Example 13

8-(Hexahydropyrrolo[3,4-b]pyrrol-1-yl)-3-methyl-1,7-bis-(3,3,3-trifluoropropyl)-3,7-dihydro-purine-2,6-dione hydrochloride MS: M+1=469

Example 14

8-(Hexahydropyrrolo[3,4-b]pyrrol-1-yl)-1-(2-hydroxy-2-phenylethyl)-3-methyl-7-(3-methyl-but-2-enyl)-3,7-dihydropurine-2,6-dione hydrochloride MS: M+1=465

Example 15

3-Ethyl-8-(hexahydropyrrolo[3,4-b]pyrrol-1-yl)-7-(3-methylbut-2-enyl)-1-(2-oxo-2-phenyl-ethyl)-3,7-dihydropurine-2,6-dione hydrochloride MS: M+1=477

Example 16

1-(5-Fluorobenzothiazol-2-ylmethyl)-8-(hexahydropyrrolo[3,4-b]pyrrol 1-yl)-3-methyl-7-(3-methylbut-2-enyl)-3,7-dihydropurine-2,6-dione hydrochloride MS: M+1=510

Example 17

1-(5-Cyclopropyl[1,3,4]thiadiazol-2-ylmethyl)-8-(hexahydropyrrolo[3,4-b]pyrrol-1-yl)-3-methyl-7-(3-methylbut-2-enyl)-3,7-dihydropurine-2,6-dione hydrochloride MS: M+1=483

Example 18

8-(Hexahydropyrrolo[3,4-b]pyrrol-1-yl)-1,3,7-trimethyl-3,7-dihydropurine-2,6-dione hydrochloride MS: M+1=305

Example 19

8-(Hexahydropyrrolo[3,4-b]pyrrol-1-yl)-1,3-dimethyl-7-(3-methylbut-2-enyl)-3,7-dihydropurine-2,6-dione hydrochloride MS: M+1=359

Example 20

3-Cyclopropyl-8-(hexahydropyrrolo[3,4-b]pyrrol-1-yl)-7-(3-methylbut-2-enyl)-1-(2-oxo-2-phenylethyl)-3,7-dihydropurine-2,6-dione hydrochloride MS: M+1=489

Example 21

3-Cyclopropyl-8-(hexahydropyrrolo[3,4-b]pyrrol-1-yl)-7-(3-methylbut-2-enyl)-1-phenethyl-3,7-dihydropurine-2,6-dione hydrochloride MS: M+1=475

Example 22

7-(2-Chloro-4-fluorobenzyl)-8-(hexahydropyrrolo[3,4-b]pyrrol-1-yl)-1,3-dimethyl-3,7-dihydropurine 2,6-dione hydrochloride MS: M+1=433

Example 23

7-But-2-ynyl-8-(hexahydropyrrolo[3,4-b]pyrrol-1-yl)-3-methyl-1-(2-oxo-2-phenylethyl)-3,7-dihydropurine-2,6-dione trifluoroacetate MS: M+1=447

Example 24

1-[2-(4-Bromophenyl)-2,2-difluoroethyl]-8-(S,S-hexahydropyrrolo[3,4-b]pyrrol-5-yl)-3-methyl-7-(3-methylbut-2-enyl)-3,7-dihydropurine-2,6-dione trifluoroacetate MS: M+1=564

Example 25

1-[2-(4-Bromophenyl)-2,2-difluoroethyl]-8-(R,R-hexahydropyrrolo[3,4-b]pyrrol-5-yl)-3-methyl-7-(3-methylbut-2-enyl)-3,7-dihydropurine-2,6-dione trifluoroacetate MS: M+1=564

Example 26

1-[2,2-Difluoro-2-(4-fluorophenyl)ethyl]-8-(S,S-hexahydropyrrolo[3,4-b]pyrrol-1-yl)-3-methyl-7-(3-methylbut-2-enyl)-3,7-dihydropurine-2,6-dione trifluoroacetate MS: M+1=503

Example 27

1-[2,2-Difluoro-2-(4-fluorophenyl)ethyl]-8-(R,R-hexahydropyrrolo[3,4-b]pyrrol-1-yl)-3-methyl-7-(3-methylbut-2-enyl)-3,7-dihydropurine-2,6-dione trifluoroacetate MS: M+1=503

Example 28

3-Ethyl-8-(hexahydropyrrolo[3,4-b]pyrrol-1-yl)-1-(3-hydroxy-3-methylbutyl)-7-(3-methylbut-2-enyl)-3,7-dihydropurine-2,6-dione trifluoroacetate MS: M+1=445

Example 29

7-But-2-ynyl-1-(3,3-dimethyl-2-oxobutyl)-8-(hexahydropyrrolo[3,4-b]pyrrol-1-yl)-3-methyl-3,7-dihydropurine-2,6-dione trifluoroacetate MS: M+1=427

Example 30

8-(H exahydropyrrolo[3,4-b]pyrrol-1-yl)-1,3-dimethyl-7-(2-oxo-2-phenylethyl)-3,7-dihydro-purine-2,6-dione hydrochloride MS: M+1=409

Example 31

1-(1-Benzyl-1H-imidazol-2-ylmethyl)-8-(hexahydropyrrolo[3,4-b]pyrrol-1-yl)-3-methyl-7-(3-methylbut-2-enyl)-3,7-dihydropurine-2,6-dione MS: M+1=515

Example 32

2-[8-(Hexahydropyrrolo[3,4-b]pyrrol-1-yl)-1,3-dimethyl-2,6-dioxo-1,2,3,6-tetrahydropurine-7-ylmethyl]benzonitrile trifluoroacetate MS: M+1=406

Example 33

8-(Hexahydropyrrolo[3,4-b]pyrrol-1-yl)-1,3-dimethyl-7-(3-phenylallyl)-3,7-dihydropurine-2,6-dione trifluoroacetate MS: M+1=407

Example 34

8-(Hexahydropyrrolo[3,4-b]pyrrol-1-yl)-7-(3-methylbut-2-enyl)-1-(2-oxo-2-phenylethyl)-3-(2,2,2-trifluoroethyl)-3,7-dihydropurine-2,6-dione trifluoroacetate MS: M+1=515

Example 35

8-(Hexahydropyrrolo[3,4-b]pyrrol-1-yl)-7-(3-methylbut-2-enyl)-1-(2-oxo-2-phenylethyl)-3-(2,2,2-trifluoroethyl)-3,7-dihydropurine-2,6-dione hydrochloride MS: M+1=531

Example 36

8-(S,S-Hexahydropyrrolo[3,4-b]pyrrol-1-yl)-1-(S-2-hydroxy-2-phenylethyl)-3-methyl-7-(3-methylbut-2-enyl)-3,7-dihydropurine-2,6-dione trifluoroacetate MS: M+1=465

Example 37

8-(R,R-Hexahydropyrrolo[3,4-b]pyrrol-1-yl)-1-(S-2-hydroxy-2-phenylethyl)-3-methyl-7-(3-methylbut-2-enyl)-3,7-dihydropurine-2,6-dione trifluoroacetate MS: M+1=465

Example 38

8-(S,S-Hexahydropyrrolo[3,4-b]pyrrol-1-yl)-1-(R-2-hydroxy-2-phenylethyl)-3-methyl-7-(3-methylbut-2-enyl)-3,7-dihydropurine-2,6-dione trifluoroacetate MS: M+1=465

Example 39

8-(R,R-Hexahydropyrrolo[3,4-b]pyrrol-1-yl)-1-(R-2-hydroxy-2-phenylethyl)-3-methyl-7-(3-methylbut-2-enyl)-3,7-dihydropurine-2,6-dione trifluoroacetate MS: M+1=465

Example 40

Methyl [8-(hexahydropyrrolo[3,4-b]pyrrol-1-yl)-3-methyl-2,6-dioxo-1-(2-oxo-2-phenylethyl)-1,2,3,6-tetrahydropurin-7-yl]acetate hydrochloride MS: M+1=467

Example 41

1-[2-(2-Chlorophenyl)-2-oxo-ethyl]-8-(hexahydropyrrolo[3,4-b]pyrrol-1-yl)-3-methyl-7-(3-methylbut-2-enyl)-3,7-dihydropurine-2,6-dione trifluoroacetate MS: M+1=497

Example 42

1-[2-(3-Chlorophenyl)-2-oxo-ethyl]-8-(hexahydropyrrolo[3,4-b]pyrrol-1-yl)-3-methyl-7-(3-methylbut-2-enyl)-3,7-dihydropurine-2,6-dione MS: M+1=497

Example 43

1-[2-(4-Chlorophenyl)-2-oxoethyl]-8-(hexahydropyrrolo[3,4-b]pyrrol-1-yl)-3-methyl-7-(3-methylbut-2-enyl)-3,7-dihydropurine-2,6-dione MS: M+1=497

Example 44

2-[8-(Hexahydropyrrolo[3,4-b]pyrrol-1-yl)-3-methyl-2,6-dioxo-1-(2-oxo-2-phenylethyl)-1,2,3,6-tetrahydropurin-7-yl]acetamide hydrochloride MS: M+1=452

Example 45

[8-(Hexahydropyrrolo[3,4-b]pyrrol-1-yl)-3-methyl-2,6-dioxo-1-(2-oxo-2-phenylethyl)-1,2,3,6-tetrahydropurin-7-yl]acetic acid hydrochloride MS: M+1=453

Example 46

8-(Hexahydropyrrolo[3,4-b]pyrrol-1-yl)-3-methyl-1-(2-oxo-2-phenylethyl)-7-(2-oxo-2-piperidin-1-ylethyl)-3,7-dihydropurine-2,6-dione hydrochloride MS: M+1=520

Example 47

8-(Hexahydropyrrolo[3,4-b]pyrrol-1-yl)-3-methyl-1-(2-oxo-2-phenylethyl)-7-(2-oxo-2-pyrrolidin-1-ylethyl)-3,7-dihydropurine-2,6-dione hydrochloride MS: M+1=506

Example 48

2-[8-(Hexahydropyrrolo[3,4-b]pyrrol-1-yl)-3-methyl-7-(3-methylbut-2-enyl)-2,6-dioxo-2,3,6,7-tetrahydropurin-1-yl]acetamide MS: M+1=402

Example 49

1,7-Bis(4-fluorobenzyl)-8-(hexahydropyrrolo[3,4-b]pyrrol-1-yl)-3-methyl-3,7-dihydropurine-2,6-dione trifluoroacetate MS: M+1=493

Example 50

7-(4-Fluorobenzyl)-8-(hexahydropyrrolo[3,4-b]pyrrol-1-yl)-3-methyl-1-(2-morpholin-4-yl-2-oxoethyl)-3,7-dihydropurine-2,6-dione trifluoroacetate MS: M+1=512

Example 51

1-(2-Ethoxyethyl)-7-(4-fluorobenzyl)-8-(hexahydropyrrolo[3,4-b]pyrrol-1-yl)-3-methyl-3,7-dihydropurine-2,6-dione trifluoroacetate MS: M+1=457

Example 52

7-(4-Fluorobenzyl)-8-(hexahydropyrrolo[3,4-b]pyrrol-1-yl)-3-methyl-1-(3-methylbutyl)-3,7-dihydropurine-2,6-dione trifluoroacetate MS: M+1=455

Example 53

2-[7-(4-Fluorobenzyl)-8-(hexahydropyrrolo[3,4-b]pyrrol-1-yl)-3-methyl-2,6-dioxo-2,3,6,7-tetrahydropurin-1-yl]-N-indan-2-ylacetamide trifluoroacetate MS: M+1=558

Example 54

2-[7-(2-Chlorobenzyl)-8-(hexahydropyrrolo[3,4-b]pyrrol-1-yl)-3-methyl-2,6-dioxo-2,3,6,7-tetrahydropurin-1-yl]-N-(2,4-dichlorophenyl)acetamide trifluoroacetate S: M+1=602

Example 55

7-(2-Chlorobenzyl)-8-(hexahydropyrrolo[3,4-b]pyrrol-1-yl)-3-methyl-1-(2-morpholin-4-yl-2-oxoethyl)-3,7-dihydropurine-2,6-dione trifluoroacetate MS: M+1=528

Example 56

7-(2-Chlorobenzyl)-1-(2-ethoxyethyl)-8-(hexahydropyrrolo[3,4-b]pyrrol-1-yl)-3-methyl-3,7-dihydropurine-2,6-dione trifluoroacetate MS: M+1=473

Example 57

7-(2-Chlorobenzyl)-8-(hexahydropyrrolo[3,4-b]pyrrol-1-yl)-3-methyl-1-(3-methylbutyl)-3,7-dihydropurin-2,6-dione trifluoroacetate MS: M+1=471

Example 58

1-(2-Adamantan-1-yl-2-oxoethyl)-7-(2-chlorobenzyl)-8-(hexahydropyrrolo[3,4-b]pyrrol-1-yl)-3-methyl-3,7-dihydropurine-2,6-dione trifluoroacetate MS: M+1=577

Example 59

7-(2-Chlorobenzyl)-8-(hexahydropyrrolo[3,4-b]pyrrol-1-yl)-3-methyl-1-(2-phenoxyethyl)-3,7-dihydropurine-2,6-dione trifluoroacetate MS: M+1=521

Example 60

2-[7-(2-Chlorobenzyl)-8-(hexahydropyrrolo[3,4-b]pyrrol-1-yl)-3-methyl-2,6-dioxo-2,3,6,7-tetrahydropurin-1-yl]-N-indan-2-ylacetamide trifluoroacetate MS: M+1=574

Example 61

8-(Hexahydropyrrolo[3,4-b]pyrrol-1-yl)-1,3-dimethyl-7-(3-trifluormethylbenzyl)-3,7-dihydro-purine-2,6-dione trifluoroacetate MS: M+1=449

Example 62

8-(Hexahydropyrrolo[3,4-b]pyrrol-1-yl)-3-methyl-1-(2-morpholin-4-yl-2-oxoethyl)-7-(3-trifluoromethylbenzyl)-3,7-dihydropurine-2,6-dione trifluoroacetate MS: M+1=562

Example 63

1-(2-Ethoxyethyl)-8-(hexahydropyrrolo[3,4-b]pyrrol-1-yl)-3-methyl-7-(3-trifluoromethylbenzyl)-3,7-dihydropurine-2,6-dione trifluoroacetate MS: M+1=507

Example 64

1-(2-Adamantan-1-yl-2-oxoethyl)-8-(hexahydropyrrolo[3,4-b]pyrrol-1-yl)-3-methyl-7-(3-phenylallyl)-3,7-dihydropurine-2,6-dione trifluoroacetate MS: M+1=569

Example 65

8-(Hexahydropyrrolo[3,4-b]pyrrol-1-yl)-3-methyl-1,7-bis(3-methylbutyl)-3,7-dihydropurine-2,6-dione trifluoroacetate MS: M+1=417

Example 66

8-(Hexahydropyrrolo[3,4-b]pyrrol-1-yl)-3-methyl-7-(3-methylbutyl)-1-(2-phenoxyethyl)-3,7-dihydropurine-2,6-dione-trifluoroacetate MS: M+1=467

Example 67

1-[2-(4-Fluorophenyl)ethyl]-8-(hexahydropyrrolo[3,4-b]pyrrol-1-yl)-3-methyl-7-(3-methyl-butyl)-3,7-dihydropurine-2,6-dione trifluoroacetate MS: M+1=469

Example 68

7-[2-(4-Fluorophenyl)ethyl]-8-(hexahydropyrrolo[3,4-b]pyrrol-1-yl)-1,3-dimethyl-3,7-dihydro-purine-2,6-dione trifluoroacetate MS: M+1=413

Example 69

1-(4-Fluorobenzyl)-7-[2-(4-fluorophenyl)ethyl]-8-(hexahydropyrrolo[3,4-b]pyrrol-1-yl)-3-methyl-3,7-dihydropurine-2,6-dione trifluoroacetate MS: M+1=507

Example 70

7-[2-(4-Fluorophenyl)ethyl]-8-(hexahydropyrrolo[3,4-b]pyrrol-1-yl)-3-methyl-1-(2-morpholin-4-yl-2-oxoethyl)-3,7-dihydropurine-2,6-dione trifluoroacetate MS: M+1=526

Example 71

1-(2-Ethoxyethyl)-7-[2-(4-fluorophenyl)ethyl]-8-(hexahydropyrrolo[3,4-b]pyrrol-1-yl)-3-methyl-3,7-dihydropurine-2,6-dione trifluoroacetate MS: M+1=471

Example 72

7-[2-(4-Fluorophenyl)ethyl]-8-(hexahydropyrrolo[3,4-b]pyrrol-1-yl)-3-methyl-1-(3-methyl-butyl)-3,7-dihydropurine-2,6-dione trifluoroacetate MS: M+1=469

Example 73

1-(2-Adamantan-1-yl-2-oxoethyl)-7-[2-(4-fluorophenyl)ethyl]-8-(hexahydropyrrolo[3,4-b]pyrrol-1-yl)-3-methyl-3,7-dihydropurine-2,6-dione trifluoroacetate MS: M+1=575

Example 74

7-[2-(4-Fluorophenyl)ethyl]-8-(hexahydropyrrolo[3,4-b]pyrrol-1-yl)-3-methyl-1-(2-phenoxy-ethyl)-3,7-dihydropurine-2,6-dione trifluoroacetate MS: M+1=519

Example 75

2-[7-[2-(4-Fluorophenyl)ethyl]-8-(hexahydropyrrolo[3,4-b]pyrrol-1-yl)-3-methyl-2,6-dioxo-2,3,6,7-tetrahydropurin-1-yl]-N-indan-2-ylacetamide trifluoroacetate MS: M+1=572

Example 76

8-(Hexahydropyrrolo[3,4-b]pyrrol-1-yl)-1,3-dimethyl-7-oxazol-2-ylmethyl-3,7-dihydropurine-2,6-dione trifluoroacetate MS: M+1=372

Example 77

1-(4-Fluorobenzyl)-8-(hexahydropyrrolo[3,4-b]pyrrol-1-yl)-3-methyl-7-oxazol-2-ylmethyl-3,7-dihydropurine-2,6-dione trifluoroacetate MS: M+1=466

Example 78

N-(2,4-Dichlorophenyl)-2-[8-(hexahydropyrrolo[3,4-b]pyrrol-1-yl)-3-methyl-7-oxazol-2-ylmethyl-2,6-dioxo-2,3,6,7-tetrahydropurin-1-yl]acetamide trifluoroacetate MS: M+1=559

Example 79

1-(2-Ethoxyethyl)-8-(hexahydropyrrolo[3,4-b]pyrrol-1-yl)-3-methyl-7-oxazol-2-ylmethyl-3,7-dihydropurine-2,6-dione trifluoroacetate MS: M+1=430

Example 80

8-(Hexahydropyrrolo[3,4-b]pyrrol-1-yl)-3-methyl-1-(3-methylbutyl)-7-oxazol-2-ylmethyl-3,7-dihydropurine-2,6-dione trifluoroacetate MS: M+1=428

Example 81

1-(2-Adamantan-1-yl-2-oxoethyl)-8-(hexahydropyrrolo[3,4-b]pyrrol-1-yl)-3-methyl-7-oxazol-2-ylmethyl-3,7-dihydropurine-2,6-dione trifluoroacetate MS: M+1=534

Example 82

8-(Hexahydropyrrolo[3,4-b]pyrrol-1-yl)-3-methyl-7-oxazol-2-ylmethyl-1-(2-phenoxyethyl)-3,7-dihydropurine-2,6-dione trifluoroacetate MS: M+1=478

Example 83

1-[2-(4-Fluorophenyl)ethyl]-8-(hexahydropyrrolo[3,4-b]pyrrol-1-yl)-3-methyl-7-oxazol-2-ylmethyl-3,7-dihydropurine-2,6-dione trifluoroacetate MS: M+1=480

Example 84

2-[8-(Hexahydropyrrolo[3,4-b]pyrrol-1-yl)-3-methyl-7-oxazol-2-ylmethyl-2,6-dioxo-2,3,6,7-tetrahydropurin-1-yl]-N-indan-2-ylacetamide trifluoroacetate MS: M+1=531

Example 85

8-(Hexahydropyrrolo[3,4-b]pyrrol-1-yl)-3-methyl-7-(3-methylbut-2-enyl)-1-(2-methyl-2H-tetrazol-5-ylmethyl)-3,7-dihydropurine-2,6-dione trifluoroacetate MS: M+1=441

Example 86

8-(Hexahydropyrrolo[3,4-b]pyrrol-1-yl)-3-methyl-7-(3-methylbut-2-enyl)-1-(1-methyl-1H-tetrazol-5-ylmethyl)-3,7-dihydropurine-2,6-dione trifluoroacetate MS: M+1=441

Example 87

8-(Hexahydropyrrolo[3,4-b]pyrrol-1-yl)-3-methyl-1-(3-methylbutyl)-7-(3-trifluoromethylbenzyl)-3,7-dihydropurine-2,6-dione trifluoroacetate MS: M+1=505

Example 88

1-(2-Adamantan-1-yl-2-oxoethyl)-8-(hexahydropyrrolo[3,4-b]pyrrol-1-yl)-3-methyl-7-(3-trifluoromethylbenzyl)-3,7-dihydropurine-2,6-dione trifluoroacetate MS: M+1=611

Example 89

8-(Hexahydropyrrolo[3,4-b]pyrrol-1-yl)-3-methyl-1-(2-phenoxyethyl)-7-(3-trifluoromethyl-benzyl)-3,7-dihydropurine-2,6-dione trifluoroacetate MS: M+1=555

Example 90

8-(Hexahydropyrrolo[3,4-b]pyrrol-1-yl)-3-methyl-1-(2-morpholin-4-yl-2-oxoethyl)-7-(3-phenylallyl)-3,7-dihydropurine-2,6-dione trifluoroacetate MS: M+1=520

Example 91

1-(2-Ethoxyethyl)-8-(hexahydropyrrolo[3,4-b]pyrrol-1-yl)-3-methyl-7-(3-phenylallyl)-3,7-dihydropurine-2,6-dione trifluoroacetate MS: M+1=465

Example 92

7-(4-Fluorobenzyl)-8-(hexahydropyrrolo[3,4-b]pyrrol-1-yl)-1,3-dimethyl-3,7-dihydropurine-2,6-dione trifluoroacetate MS: M+1=399

Example 93

N-(2,4-Dichlorophenyl)-2-[7-(4-fluorobenzyl)-8-(hexahydropyrrolo[3,4-b]pyrrol-1-yl)-3-methyl-2,6-dioxo-2,3,6,7-tetrahydropurin-1-yl]acetamide trifluoroacetate MS: M+1=586

Example 94

1-(2-Adamantan-1-yl-2-oxoethyl)-7-(4-fluorobenzyl)-8-(hexahydropyrrolo[3,4-b]pyrrol-1-yl)-3-methyl-3,7-dihydropurine-2,6-dione trifluoroacetate MS: M+1=561

Example 95

7-(4-Fluorobenzyl)-1-[2-(4-fluorophenyl)ethyl]-8-(hexahydropyrrolo[3,4-b]pyrrol-1-yl)-3-methyl-3,7-dihydropurine-2,6-dione trifluoroacetate MS: M+1=507

Example 96

1-Cyclopentyl-7-(4-fluorobenzyl)-8-(hexahydropyrrolo[3,4-b]pyrrol-1-yl)-3-methyl-3,7-dihydropurine-2,6-dione trifluoroacetate MS: M+1=453

Example 97

7-(2-Chlorobenzyl)-8-(hexahydropyrrolo[3,4-b]pyrrol-1-yl)-1,3-dimethyl-3,7-dihydropurine-2,6-dione trifluoroacetate MS: M+1=415

Example 98

7-(2-Chlorobenzyl)-1-(4-fluorobenzyl)-8-(hexahydropyrrolo[3,4-b]pyrrol-1-yl)-3-methyl-3,7-dihydropurine-2,6-dione trifluoroacetate MS: M+1=509

Example 99

7-(2-Chlorobenzyl)-1-[2-(4-fluorophenyl)ethyl]-8-(hexahydropyrrolo[3,4-b]pyrrol-1-yl)-3-methyl-3,7-dihydropurine-2,6-dione trifluoroacetate MS: M+1=523

Example 100

7-(2-Chlorobenzyl)-1-cyclopentyl-8-(hexahydropyrrolo[3,4-b]pyrrol-1-yl)-3-methyl-3,7-dihydropurine-2,6-dione trifluoroacetate MS: M+1=469

Example 101

1-Cyclopentyl-8-(hexahydropyrrolo[3,4-b]pyrrol-1-yl)-3-methyl-7-(3-trifluoromethylbenzyl)-3,7-dihydropurine-2,6-dione trifluoroacetate MS: M+1=503

Example 102

2-[8-(Hexahydropyrrolo[3,4-b]pyrrol-1-yl)-3-methyl-2,6-dioxo-7-(3-trifluoromethylbenzyl)-2,3,6,7-tetrahydropurin-1-yl]-N-indan-2-ylacetamide trifluoroacetate MS: M+1=608

Example 103

7-Cyclohexylmethyl-8-(hexahydropyrrolo[3,4-b]pyrrol-1-yl)-1,3-dimethyl-3,7-dihydro purine-2,6-dione-trifluoroacetate MS: M+1=387

Example 104

7-Cyclohexylmethyl-1-(4-fluoro-benzyl)-8-(hexahydropyrrolo[3,4-b]pyrrol-1-yl)-3-methyl-3,7-dihydropurine-2,6-dione trifluoroacetate MS: M+1=481

Example 105

7-Cyclohexylmethyl-8-(hexahydropyrrolo[3,4-b]pyrrol-1-yl)-3-methyl-1-(2-morpholin-4-yl-2-oxoethyl)-3,7-dihydropurine-2,6-dione trifluoroacetate MS: M+1=500

Example 106

7-Cyclohexylmethyl-1-(2-ethoxyethyl)-8-(hexahydropyrrolo[3,4-b]pyrrol-1-yl)-3-methyl-3,7-dihydropurine-2,6-dione trifluoroacetate MS: M+1=445

Example 107

7-Cyclohexylmethyl-8-(hexahydropyrrolo[3,4-b]pyrrol-1-yl)-3-methyl-1-(3-methylbutyl)-3,7-dihydropurine-2,6-dione trifluoroacetate MS: M+1=443

Example 108

7-Cyclohexylmethyl-8-(hexahydropyrrolo[3,4-b]pyrrol-1-yl)-3-methyl-1-(2-phenoxyethyl)-3,7-dihydropurine-2,6-dione trifluoroacetate MS: M+1=493

Example 109

7-Cyclohexylmethyl-1-[2-(4-fluorophenyl)ethyl]-8-(hexahydropyrrolo[3,4-b]pyrrol-1-yl)-3-methyl-3,7-dihydropurine-2,6-dione trifluoroacetate MS: M+1=495

Example 110

2-[8-(Hexahydropyrrolo[3,4-b]pyrrol-1-yl)-3-methyl-2,6-dioxo-7-(3-phenylallyl)-2,3,6,7-tetrahydropurin-1-yl]-N-indan-2-ylacetamide trifluoroacetate MS: M+1=566

Example 111

1-(4-Fluorobenzyl)-8-(hexahydropyrrolo[3,4-b]pyrrol-1-yl)-3-methyl-7-(3-methylbutyl)-3,7-dihydropurine-2,6-dione trifluoroacetate MS: M+1=455

Example 112

N-(2,4-Dichlorophenyl)-2-[8-(hexahydropyrrolo[3,4-b]pyrrol-1-yl)-3-methyl-7-(3-methylbutyl)-2,6-dioxo-2,3,6,7-tetrahydropurin-1-yl]acetamide trifluoroacetate MS: M+1=548

Example 113

8-(Hexahydropyrrolo[3,4-b]pyrrol-1-yl)-3-methyl-7-(3-methylbutyl)-1-(2-morpholin-4-yl-2-oxoethyl)-3,7-dihydropurine-2,6-dione trifluoroacetate MS: M+1=474

Example 114

1-(2-Ethoxyethyl)-8-(hexahydropyrrolo[3,4-b]pyrrol-1-yl)-3-methyl-7-(3-methylbutyl)-3,7-dihydropurine-2,6-dione trifluoroacetate MS: M+1=419

Example 115

1-Cyclopentyl-8-(hexahydropyrrolo[3,4-b]pyrrol-1-yl)-3-methyl-7-(3-methylbutyl)-3,7-dihydropurine-2,6-dione trifluoroacetate MS: M+1=415

Example 116

2-[8-(Hexahydropyrrolo[3,4-b]pyrrol-1-yl)-3-methyl-7-(3-methylbutyl)-2,6-dioxo-2,3,6,7-tetrahydropurin-1-yl]-N-indan-2-ylacetamide trifluoroacetate MS: M+1=520

Example 117

2-[8-(Hexahydropyrrolo[3,4-b]pyrrol-1-yl)-1,3-dimethyl-2,6-dioxo-1,2,3,6-tetrahydropurin-7-yl]-N-isopropylacetamide trifluoroacetate MS: M+1=390

Example 118

8-(Hexahydropyrrolo[3,4-b]pyrrol-1-yl)-3-methyl-1-(2-morpholin-4-yl-2-oxoethyl)-7-oxazol-2-ylmethyl-3,7-dihydropurine-2,6-dione trifluoroacetate MS: M+1=485

Example 119

1-Cyclopentyl-8-(hexahydropyrrolo[3,4-b]pyrrol-1-yl)-3-methyl-7-oxazol-2-ylmethyl-3,7-dihydropurine-2,6-dione trifluoroacetate MS: M+1=426

Example 120

8-(Hexahydropyrrolo[3,4-b]pyrrol-1-yl)-3-methyl-7-(2-methyl-2H-tetrazol-5-ylmethyl)-1-(2-oxo-2-phenylethyl)-3,7-dihydropurine-2,6-dione trifluoroacetate MS: M+1=491

Example 121

[8-(Hexahydropyrrolo[3,4-b]pyrrol-1-yl)-3-methyl-7-(3-methylbut-2-enyl)-2,6-dioxo-2,3,6,7-tetrahydropurin-1-yl]acetonitrile trifluoroacetate MS: M+1=384

Example 122

[8-(Hexahydropyrrolo[3,4-b]pyrrol-1-yl)-3-methyl-2,6-dioxo-1-(2-oxo-2-phenylethyl)-1,2,3,6-tetrahydropurin-7-yl]acetonitrile trifluoroacetate MS: M+1=434

Example 123

8-[5-(4-Bromobenzoyl)hexahydropyrrolo[3,4-b]pyrrol-1-yl]-3-methyl-7-(3-methylbut-2-enyl)-1-(2-oxo-2-phenylethyl)-3,7-dihydropurine-2,6-dione MS: M+1=646

Example 124

8-(Hexahydropyrrolo[3,4-b]pyrrol-1-yl)-3-methyl-7-(3-methylbut-2-enyl)-1-(5-phenyl-[1,3,4]oxadiazol-2-ylmethyl)-3,7-dihydropurine-2,6-dione trifluoroacetate MS: M+1=503

Example 125

8-(Hexahydropyrrolo[3,4-b]pyrrol-1-yl)-3-methyl-7-(5-methyl[1,3,4]oxadiazol-2-ylmethyl)-1-(2-oxo-2-phenylethyl)-3,7-dihydropurine-2,6-dione trifluoroacetate MS: M+1=491

Example 126

2-[8-(Hexahydropyrrolo[3,4-b]pyrrol-1-yl)-3-methyl-2,6-dioxo-1-(2-oxo-2-phenylethyl)-1,2,3,6-tetrahydropurin-7-yl]-N-isopropylacetamide hydrochloride MS: M+1=494

Example 127

N-Benzyl-2-[8-(hexahydropyrrolo[3,4-b]pyrrol-1-yl)-3-methyl-2,6-dioxo-1-(2-oxo-2-phenyl-ethyl)-1,2,3,6-tetrahydropurin-7-yl]acetamide hydrochloride MS: M+1=542

Example 128

2-[8-(Hexahydropyrrolo[3,4-b]pyrrol-1-yl)-3-methyl-2,6-dioxo-1-(2-oxo-2-phenylethyl)-1,2,3,6-tetrahydropurin-7-yl]-N-(2-hydroxyethyl)acetamide hydrochloride MS: M+1=496

Example 129

8-(Hexahydropyrrolo[3,4-b]pyrrol-1-yl)-3-methyl-7-(2-morpholin-4-yl-2-oxoethyl)-1-(2-oxo-2-phenylethyl)-3,7-dihydropurine-2,6-dione hydrochloride MS: M+1=522

Example 130

2-[8-(Hexahydropyrrolo[3,4-b]pyrrol-1-yl)-3-methyl-2,6-dioxo-1-(2-oxo-2-phenylethyl)-1,2,3,6-tetrahydropurin-7-yl]-N,N-dimethylacetamide hydrochloride MS: M+1=480

Example 131

Ethyl 2-{2-[8-(hexahydropyrrolo[3,4-b]pyrrol-1-yl)-3-methyl-7-(3-methylbut-2-enyl)-2,6-dioxo-2,3,6,7-tetrahydropurin-1-yl]acetyl}benzoate trifluoroacetate MS: M+1=535

Example 132

1,7-bis(2,5-Difluorobenzyl)-8-(hexahydropyrrolo[3,4-b]pyrrol-1-yl)-3-methyl-3,7-dihydropurine-2,6-dione trifluoroacetate MS: M+1=529

Example 133

7-(2-Chlorobenzyl)-3-[2-(4-fluorophenyl)ethyl]-8-(hexahydropyrrolo[3,4-b]pyrrol-1-yl)-1-methyl-3,7-dihydropurine-2,6-dione trifluoroacetate MS: M+1=523

Example 134

7-(2-Chlorobenzyl)-3-[2-(4-fluorophenyl)ethyl]-8-(hexahydropyrrolo[3,4-b]pyrrol-1-yl)-1-(2-morpholin-4-yl-2-oxoethyl)-3,7-dihydropurine-2,6-dione; compound with trifluoroacetic acid
MS: M+1=637

Example 135

N-(2,4-Dichlorophenyl)-2-[3-[2-(4-fluorophenyl)ethyl]-8-(hexahydropyrrolo[3,4-b]pyrrol-1-yl)-7-(3-methylbutyl)-2,6-dioxo-2,3,6,7-tetrahydropurin-1-yl]acetamide; compound with trifluoroacetic acid
MS: M+1=656

Example 136

7-(2-Chlorobenzyl)-8-(hexahydropyrrolo[3,4-b]pyrrol-1-yl)-1-methyl-3-(2,2,2-trifluoroethyl)-3,7-dihydropurine-2,6-dione trifluoroacetate
MS: M+1=483

Example 137

1-Cyclopentyl-8-(hexahydropyrrolo[3,4-b]pyrrol-1-yl)-3-(2,2,2-trifluoroethyl)-7-(3-trifluoromethylbenzyl)-3,7-dihydropurine-2,6-dione; compound with trifluoroacetic acid
MS: M+1=571

Example 138

7-Cyclohexylmethyl-1-(2-ethoxyethyl)-8-(hexahydropyrrolo[3,4-b]pyrrol-1-yl)-3-(2,2,2-trifluoroethyl)-3,7-dihydropurine-2,6-dione trifluoroacetate
MS: M+1=513

Example 139

N-(2,4-Dichlorophenyl)-2-[8-(hexahydropyrrolo[3,4-b]pyrrol-1-yl)-7-oxazol-2-ylmethyl-2,6-dioxo-3-(2,2,2-trifluoroethyl)-2,3,6,7-tetrahydropurin-1-yl]acetamide; compound with trifluoroacetic acid
MS: M+1=627

Example 140

8-(Hexahydropyrrolo[3,4-b]pyrrol-1-yl)-3-methyl-1-(2-oxo-2-phenylethyl)-7-(2,4,5-trifluoro-benzyl)-3,7-dihydropurine-2,6-dione; compound with trifluoroacetic acid
MS: M+1=539

Example 141

2-[8-(Hexahydropyrrolo[3,4-b]pyrrol-1-yl)-3-methyl-2,6-dioxo-1-(2-oxo-2-phenylethyl)-1,2,3,6-tetrahydropurin-7-ylmethyl]benzonitrile trifluoroacetate
MS: M+1=510

Example 142

7-(2-Chlorobenzyl)-3-cyclopropyl-1-(2-ethoxyethyl)-8-(hexahydropyrrolo[3,4-b]pyrrol-1-yl)-3,7-dihydropurine-2,6-dione trifluoroacetate
MS: M+1=499

Example 143

1-(2-Adamantan-1-yl-2-oxoethyl)-3-cyclopropyl-8-(hexahydropyrrolo[3,4-b]pyrrol-1-yl)-7-(3-methylbutyl)-3,7-dihydropurine-2,6-dione trifluoroacetate
MS: M+1=549

Example 144

2-[3-Cyclopropyl-8-(hexahydropyrrolo[3,4-b]pyrrol-1-yl)-7-oxazol-2-ylmethyl-2,6-dioxo-2,3,6,7-tetrahydropurin-1-yl]-N-(2,4-dichlorophenyl)acetamide trifluoroacetate
MS: M+1=585

Example 145

3-Cyclopropyl-8-(hexahydropyrrolo[3,4-b]pyrrol-1-yl)-7-oxazol-2-ylmethyl-1-(2-phenoxy-ethyl)-3,7-dihydropurine-2,6-dione trifluoroacetate
MS: M+1=504

Example 146

8-(Hexahydropyrrolo[3,4-b]pyrrol-1-yl)-3-methyl-1-(2-oxo-2-phenylethyl)-7-(2-trifluoromethoxybenzyl)-3,7-dihydropurine-2,6-dione hydrochloride
MS: M+1=569

Example 147

7-(4-Chloro-2-methanesulfonylbenzyl)-8-(hexahydropyrrolo[3,4-b]pyrrol-1-yl)-3-methyl-1-(2-oxo-2-phenylethyl)-3,7-dihydropurine-2,6-dione hydrochloride
MS: M+1=597

What is claimed is:

1. A compound of the formula I,

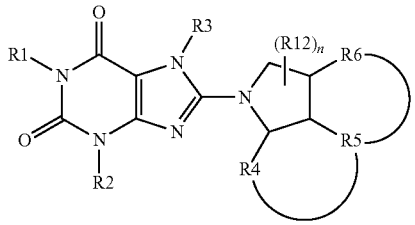

wherein:

R1, R2 and R3 are independently selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, and heterocycle, where the alkyl, cycloalkyl, alkenyl, alkynyl, aryl and heterocycle groups may be substituted one or more times by F, Cl, Br, I, CN, $NO_2$, SH, OH, $(C_1-C_6)$-alkyl, $—CF_3$, $—OCF_3$, $—SCF_3$, $(C_2-C_6)$-alkenyl, $(C_2-C_6)$-alkynyl, OR7, OP(O)(OR7)$_2$, NR7R8, NR7CONR7R8, COR7, OCOR7, OCOOR7, COOR7, CONR7R8, OCONR7R8, $(C_1-C_6)$-alkylene-OR7, $(C_1-C_6)$-alkylene-NR7R8, $(C_1-C_6)$-alkylene-NR7SO$_2$R7, $(C_1-C_6)$-alkylene-SR7, alkylene-S(O)R7, alkylene-S(O)$_2$R7, alkylene-S(O)$_2$NR7R8, $(C_1-C_6)$-alkylene-COR7, $(C_1-C_6)$-alkylene-COOR7, $(C_1-C_6)$-alkylene-CONR7R8, SR7, SOR7, SO$_2$R7, SO$_2$NR7R8, NR7SO$_2$R7, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocycle, $(C_3-C_{10})$-cycloalkyl, $(C_6-C_{10})$-aryl and heterocycle;

R7 and R8 are independently selected from the group consisting of H, $(C_1-C_6)$-alkyl, $(C_3-C_{10})$-cycloalkyl, $(C_6-C_{10})$-aryl, heterocycle, $(C_1-C_6)$-alkylene-CONR9R10, $(C_1-C_6)$-alkylene-COOR9, $(C_1-C_6)$-alkylene-COR9, $(C_1-C_6)$-alkylene-OR9, $(C_1-C_6)$-alkylene-NR9R10, $(C_1-C_6)$-alkylene-SR9, $(C_1-C_6)$-alkylene-S(O)R9, $(C_1-C_6)$-alkylene-S(O)$_2$R9, $(C_1-C_4)$-alkylene-$(C_6-C_{10})$-aryl and $(C_1-C_4)$-alkylene-heterocycle;

R9 and R10 are independently selected from the group consisting of H, $(C_1-C_6)$-alkyl, $(C_1-C_6)$-alkylene-$(C_6-C_{10})$-aryl, and $(C_1-C_6)$-alkylene-heterocycle;

R12 is selected from the group consisting of F, Cl, Br, I, $(C_1-C_6)$-alkyl, $(C_3-C_8)$-cycloalkyl, $NH_2$, $NH(C_1-C_6)$-alkyl, $NH(C_3-C_7)$-cycloalkyl, $N((C_1-C_6)$-alkyl)$_2$ and $O—(C_1-C_6)$-alkyl, where the alkyl groups may be substituted one or more times by F, Cl, Br, I;

n is 0 and wherein the portion of formula I represented by structure A

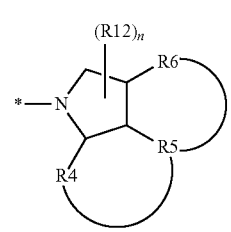

is selected from the group consisting of structures A1 to A6

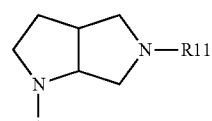
A1

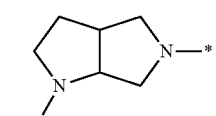
A2

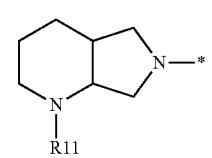
A3

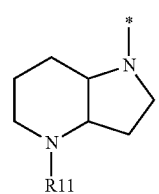
A4

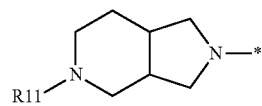
A5

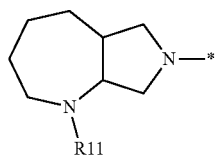
A6 where optionally the carbon atoms in structures A1 to A6 may be substituted one to four times by a moiety selected from the group consisting of F, Cl, Br, I, ($C_1$-$C_6$)-alkyl, ($C_3$-$C_8$)-cycloalkyl, $NH_2$, NH($C_1$-$C_6$)-alkyl, NH($C_3$-$C_7$)-cycloalkyl, N(($C_1$-$C_6$)-alkyl)$_2$ and O—($C_1$-$C_6$)-alkyl, and wherein optionally the alkyl groups may be substituted one or more times by F, Cl, Br, I;

R11 is selected from the group consisting of hydrogen, ($C_1$-$C_6$)-alkyl, ($C_3$-$C_8$)-cycloalkyl, ($C_1$-$C_4$)-alkylene-aryl and ($C_1$-$C_4$)-alkylene-heterocycle; and or a physiologically tolerated salt thereof.

2. A compound of the formula I as claimed in claim 1, wherein:

R1, R2 and R3 are independently selected from the group consisting of H, ($C_1$-$C_{10}$)-alkyl, ($C_3$-$C_{10}$)-cycloalkyl, ($C_2$-$C_{10}$)-alkenyl, ($C_2$-$C_{10}$)-alkynyl, ($C_6$-$C_{10}$)-aryl, and heterocycle, wherein the alkyl, cycloalkyl, alkenyl, alkynyl, aryl and heterocycle groups may be substituted one or more times by F, Cl, Br, CN, OH, ($C_1$-$C_6$)-alkyl, —$CF_3$, —$OCF_3$, —$SCF_3$, ($C_2$-$C_6$)-alkenyl, ($C_2$-$C_6$)-alkynyl, OR7, NR7R8, NR7CONR7R8, COR7, COOR7, CONR7R8, ($C_1$-$C_6$)-alkylene-OR7, ($C_1$-$C_6$)-alkylene-NR7R8, ($C_1$-$C_6$)-alkylene-NR7$SO_2$R7, ($C_1$-$C_6$)-alkylene-SR7, ($C_1$-$C_6$)-alkylene-S(O)R7, alkylene-S(O)$_2$R7, alkylene-S(O)$_2$NR7R8, ($C_1$-$C_6$)-alkylene-COR7, ($C_1$-$C_6$)-alkylene-COOR7, ($C_1$-$C_6$)-alkylene-CONR7R8, SR7, SOR7, $SO_2$R7, $SO_2$NR7R8, NR7$SO_2$R7, ($C_1$-$C_6$)-alkylene-($C_3$-$C_{10}$)-cycloalkyl, ($C_1$-$C_6$)-alkylene-($C_6$-$C_{10}$)-aryl, ($C_1$-$C_6$)-alkylene-heterocycle, ($C_3$-$C_{10}$)-cycloalkyl, ($C_6$-$C_{10}$)-aryl and heterocycle;

R7 and R8 are independently selected from the group consisting of H, ($C_1$-$C_6$)-alkyl, ($C_3$-$C_{10}$)-cycloalkyl, ($C_6$-$C_{10}$)-aryl, heterocycle, ($C_1$-$C_6$)-alkylene-CONR9R10, ($C_1$-$C_6$)-alkylene-COOR9, ($C_1$-$C_6$)-alkylene-COR9, ($C_1$-$C_6$)-alkylene-OR9, ($C_1$-$C_6$)-alkylene-NR9R10, ($C_1$-$C_4$)-alkylene-($C_6$-$C_{10}$)-aryl and ($C_1$-$C_4$)-alkylene-heterocycle;

R9 and R10 are independently selected from the group consisting of H, ($C_1$-$C_6$)-alkyl, ($C_1$-$C_6$)-alkylene-($C_6$-$C_{10}$)-aryl, and ($C_1$-$C_6$)-alkylene-heterocycle; and

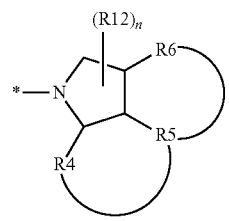
A group A of formula I
is selected from the group consisting of structures A1 to A6

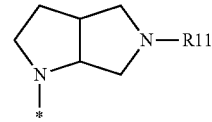
A1

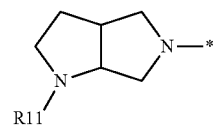
A2

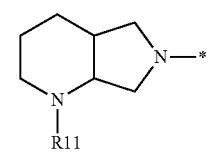
A3

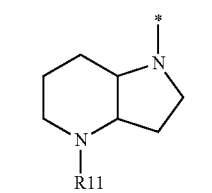
A4

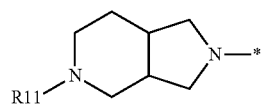
A5

-continued

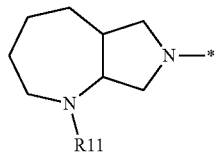

A6 wherein optionally the carbon atoms of structures A1 to A6 may be substituted one to four times by F, Cl, Br, I, $(C_1-C_6)$-alkyl, $(C_3-C_8)$-cycloalkyl, $NH_2$, $NH(C_1-C_6)$-alkyl, $NH(C_3-C_7)$-cycloalkyl, $N((C_1-C_6)$-alkyl$)_2$ or $O-(C_1-C_6)$-alkyl and where optionally the alkyl groups may be substituted one or more times by F, Cl, Br, I; and R11 is hydrogen or a physiologically tolerated salt thereof.

3. A compound as recited in claim 2, wherein;

R1, R2 and R3 are independently selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, and heterocycle, where alkyl, cycloalkyl, alkenyl, alkynyl, aryl and heterocycle radicals may be substituted one or more times by F, Cl, CN, $(C_1-C_6)$-alkyl, $-CF_3$, $-OCF_3$, $-SCF_3$, OR7, NR7R8, COR7, COOR7, CONR7R8, $(C_1-C_6)$-alkylene-OR7, $(C_1-C_6)$-alkylene-NR7R8, $(C_1-C_6)$-alkylene-NR7SO$_2$R7, SR7, SOR7, SO$_2$R7, SO$_2$NR7R8, NR7SO$_2$R7, $(C_1-C_6)$-alkylene-$(C_6-C_{10})$-aryl, $(C_1-C_6)$-alkylene-heterocycle, $(C_3-C_{10})$-cycloalkyl, $(C_6-C_{10})$-aryl and heterocycle;

R7 and R8 are independently selected from the group consisting of H, $(C_1-C_6)$-alkyl, $(C_3-C_{10})$-cycloalkyl, $(C_6-C_{10})$-alkylene-$(C_6-C_{10})$-aryl and $(C_1-C_4)$-alkylene-heterocycle; and group A of formula I

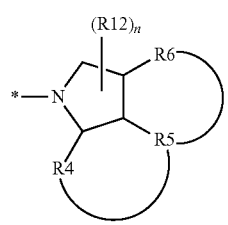

A is selected from the group consisting of structures A1 to A4

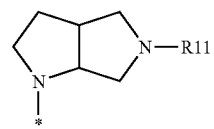

A1

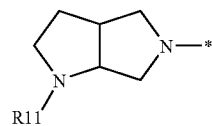

A2

-continued

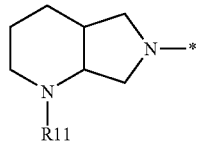

A3

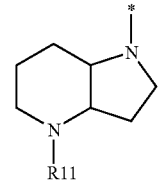

A4 where the carbon atoms in structures A1 to A4 is optionally substituted one to four times by F, Cl, Br, I, $(C_1-C_6)$-alkyl, $(C_3-C_8)$-cycloalkyl, $NH_2$, $NH(C_1-C_6)$-alkyl, $NH(C_3-C_7)$-cycloalkyl, $N((C_1-C_6)$-alkyl$)_2$ or $O-(C_1-C_6)$-alkyl, where the alkyl groups may be substituted one or more times by F, Cl, Br, I;

R11 is hydrogen; and or a physiologically tolerated salt thereof.

4. The compound as recited claim 3, wherein

R1, R2 and R3 are independently selected from the group consisting of H, $(C_1-C_{10})$-alkyl, $(C_3-C_{10})$-cyclically, $(C_2-C_{10})$-alkenyl, $(C_2-C_{10})$-alkynyl, $(C_6-C_{10})$-aryl, and heterocycle, where the alkyl, cycloalkyl, alkenyl, alkynyl, aryl and heterocycle groups may be substituted one or more times by F, Cl, CN, $(C_1-C_6)$-alkyl, $-CF_3$, $-OCF_3$, $-SCF_3$, OR7, NR7R8, COR7, COOR7, CONR7R8, $(C_1-C_6)$-alkylene-OR7, $(C_1-C_6)$-alkylene-NR7R8, $(C_1-C_6)$-alkylene-NR7SO$_2$R7, SR7, SOR7, SO$_2$R7, SO$_2$NR7R8, NR7SO$_2$R7, $(C_1-C_6)$-alkylene-$(C_6-C_{10})$-aryl, $(C_1-C_6)$-alkylene-heterocycle, $(C_3-C_{10})$-cycloalkyl, $(C_6-C_{10})$-aryl and heterocycle;

R7 and R8 are independently selected from the group consisting of H, $(C_1-C_6)$-alkyl, $(C_3-C_{10})$-cycloalkyl, $(C_6-C_{10})$-alkylene-$(C_6-C_{10})$-aryl and $(C_1-C_4)$-alkylene-heterocycle;

wherein the portion of formula I represented by structure A

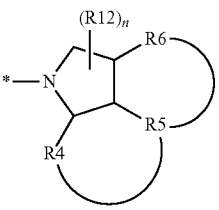

A is selected from the group consisting of structures A1, A2 or A3

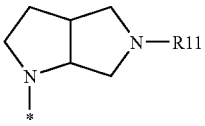

A1

-continued

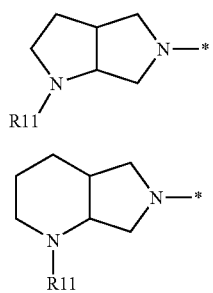

where the carbon atoms in structures A1, A2 or A3 are optionally substituted one to four times by F, Cl, Br, I, $(C_1-C_6)$-alkyl, $(C_3-C_8)$-cycloalkyl, $NH_2$, $NH(C_1-C_6)$-alkyl, $NH(C_3-C_7)$-cycloalkyl, $N((C_1-C_6)$-alkyl$)_2$ or $O-(C_1-C_6)$-alkyl and wherein the alkyl groups may optionally be substituted one or more times by F, Cl, Br, I;

R11 is hydrogen;

or a physiologically tolerated salt thereof.

5. A compound selected from the group consisting of:
8-(cis-hexahydropyrrolo[3,4-b]pyrrol-1-yl)-3-methyl-7-(3-methylbut-2-enyl)-1-(2-oxo-2-phenylethyl)-3,7-dihydropurine-2,6-dione hydrochloride;
8-(cis-hexahydropyrrolo[3,4-b]pyrrol-5-yl)-3-methyl-7-(3-methylbut-2-enyl)-1-(2-oxo-2-phenylethyl)-3,7-dihydropurine-2,6-dione; and
3-methyl-7-(3-methylbut-2-enyl)-8-(cis-octahydropyrrolo[3,4-b]pyridin-6-yl)-1-(2-oxo-2-phenylethyl)-3,7-dihydropurine-2,6-dione;

or a physiologically tolerated salt thereof.

6. A pharmaceutical composition comprising a compound of formula I

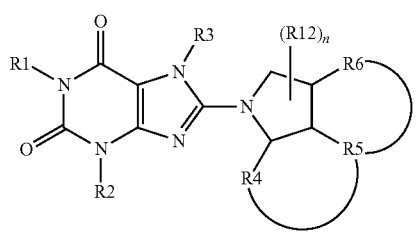

wherein:

R1, R2 and R3 are independently selected from the group consisting of H, $(C_1-C_{10})$-alkyl, $(C_3-C_{10})$-cycloalkyl, $(C_2-C_{10})$-alkenyl, $(C_2-C_{10})$-alkynyl, $(C_6-C_{10})$-aryl, and heterocycle wherein the alkyl, cycloalkyl, alkenyl, alkynyl, aryl and heterocycle groups may be substituted one or more times by F, Cl, Br, I, CN, $NO_2$, SH, OH, $(C_1-C_6)$-alkyl, $-CF_3$, $-OCF_3$, $-SCF_3$, $(C_2-C_6)$-alkenyl, $(C_2-C_6)$-alkynyl, OR7, $OP(O)(OR7)_2$, NR7R8, NR7CONR7R8, COR7, OCOR7, OCOOR7, COOR7, CONR7R8, OCONR7R8, $(C_1-C_6)$-alkylene-OR7, $(C_1-C_6)$-alkylene-NR7R8, $(C_1-C_6)$-alkylene-NR7SO$_2$R7, $(C_1-C_6)$-alkylene-SR7, alkylene-S(O)R7, alkylene-S(O)$_2$R7, alkylene-S(O)$_2$NR7R8, $(C_1-C_6)$-alkylene-COR7, $(C_1-C_6)$-alkylene-COOR7, $(C_1-C_6)$-alkylene-CONR7R8, SR7, SOR7, $SO_2$R7, $SO_2$NR7R8, NR7SO$_2$R7, $(C_1-C_6)$-alkylene-$(C_3-C_{10})$-cycloalkyl, $(C_1-C_6)$-alkylene-$(C_6-C_{10})$-aryl, $(C_1-C_6)$-alkylene-heterocycle, $(C_3-C_{10})$-cycloalkyl, $(C_6-C_{10})$-aryl and heterocycle;

R7 and R8 are independently selected from the group consisting of H, $(C_1-C_6)$-alkyl, $-CF_3$, $(C_3-C_{10})$-cycloalkyl, $(C_6-C_{10})$-aryl, $(C_6-C_{10})$-heterocycle, $(C_1-C_6)$-alkylene-CONR9R10, CONR9R10, $(C_1-C_6)$-alkylene-COOR9, COOR9, COR9, $(C_1-C_6)$-alkylene-COR9, $(C_1-C_6)$-alkylene-OR9, $(C_1-C_6)$-alkylene-NR9R10, $(C_1-C_6)$-alkylene-SR9, $(C_1-C_6)$-alkylene-S(O)R9, $(C_1-C_6)$-alkylene-S(O)$_2$R9, S(O)R9, S(O)$_2$R9, $(C_1-C_4)$-alkylene-$(C_6-C_{10})$-aryl and $(C_1-C_4)$-alkylene-heterocycle;

R9 and R10 are independently selected from the group consisting of H, $(C_1-C_6)$-alkyl, $(C_1-C_6)$-alkylene, $(C_6-C_{10})$-aryl, $(C_6-C_{10})$-aryl, $(C_6-C_{10})$-heterocycle, and $(C_1-C_6)$-alkylene-heterocycle;

R4 and R5 form together a 3-5-membered alkylene chain in which one $CH_2$ group is replaced by NR11 and wherein R6 is equal to H or R12, or R5 and R6 form together a 3 to 5-member alkylene chain in which one $CH_2$ group is replaced by NR11, where R4 is equal to H or R12; where the 3 to 5-member alkylene chain may be substituted in each case one or more times by F, Cl, Br, I, $(C_1-C_6)$-alkyl, $(C_3-C_8)$-cycloalkyl, $NH_2$, $NH(C_1-C_6)$-alkyl, $NH(C_3-C_7)$-cycloalkyl, $N((C_1-C_6)$-alkyl$)_2$ or $O-(C_1-C_6)$-alkyl, where the alkyl groups may be substituted one or more times by F, Cl, Br, I;

R11 is selected from the group consisting of hydrogen, $(C_1-C_6)$-alkyl, $(C_3-C_8)$-cycloalkyl, $(C_1-C_4)$-alkylene-aryl and $(C_1-C_4)$-alkylene-heterocycle;

R12 is selected from the group consisting of F, Cl, Br, I, $(C_1-C_6)$-alkyl, $(C_3-C_8)$-cycloalkyl, $NH_2$, $NH(C_1-C_6)$-alkyl, $NH(C_3-C_7)$-cycloalkyl, $N((C_1-C_6)$-alkyl$)_2$ and $O-(C_1-C_6)$-alkyl, where the alkyl groups may be substituted one or more times by F, Cl, Br, I;

n is 0 and wherein the portion of formula I represented by structure A comprises:

A

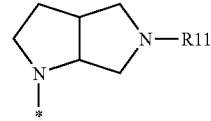

is selected from the group consisting of structures A1 to A6

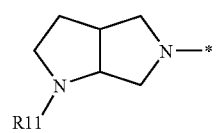

-continued

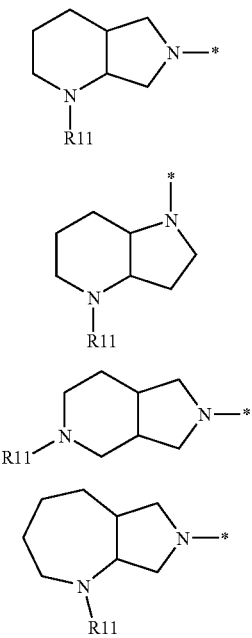

or a physiologically tolerated salt thereof in combination with one or more pharmaceutically acceptable carriers, fillers, excipients, solvents, adjuvants and mixtures thereof.

7. A pharmaceutical composition comprising a compound selected from the group consisting of:

8-(cis-hexahydropyrrolo[3,4-b]pyrrol-1-yl)-3-methyl-7-(3-methylbut-2-enyl)-1-(2-oxo-2-phenylethyl)-3,7-dihydropurine-2,6-dione hydrochloride;

8-(cis-hexahydropyrrolo[3,4-b]pyrrol-5-yl)-3-methyl-7-(3-methylbut-2-enyl)-1-(2-oxo-2-phenylethyl)-3,7-dihydropurine-2,6-dione; and 3-methyl-7-(3-methylbut-2-enyl)-8-(cis-octahydropyrrolo[3,4-b]pyridin-6-yl)-1-(2-oxo-2-phenylethyl)-3,7-dihydropurine-2,6-dione;

or a physiologically tolerated salt thereof in combination with one or more pharmaceutically acceptable carriers, fillers, excipients, solvents, adjuvants and mixtures thereof.

8. The pharmaceutical composition as recited in claim 6 wherein the at least one other active ingredient is selected from the group consisting of one or more antidiabetic agents, hypoglycemic agents, HMGCoA reductase inhibitors, cholesterol absorption inhibitors, PPAR gamma agonists, PPAR alpha agonists, PPAR alpha/gamma agonists, fibrates, MTP inhibitors, bile acid absorption inhibitors, CETP inhibitors, polymeric bile acid adsorbents, LDL receptor inducers, ACAT inhibitors, antioxidants, lipoprotein lipase inhibitors, ATP-citrate lyase inhibitors, squalene synthetase inhibitors, lipoprotein(a) antagonists, lipase inhibitors, insulins, sulfonylureas, biguanides, thiazolidinediones, α-glucosidase inhibitors, active ingredients which act on the ATP-dependent potassium channel of the beta cells, CART agonists, NPY agonists, CB-1 receptor antagonists, MCH antagonists, MC4 agonists, orexin agonists, TNF agonists, CRF agonists, CRF BP antagonists, urocortin agonists, β3 agonists, MSH (melanocyte-stimulating hormone) agonists, CCK agonists, serotonin reuptake inhibitors, mixed sertoninergic and noradrenergic compounds, 5HT agonists, bombesin agonists, galanin antagonists, growth hormones, growth hormone-releasing compounds, TRH agonists, uncoupling protein 2 or 3 modulators, leptin agonists, DA agonists, lipase/amylase inhibitors, PPAR modulators, RXR modulators or TR-β agonists, amphetamines and mixtures thereof in a pharmaceutically acceptable carrier composition.

* * * * *